(12) United States Patent
Pardee et al.

(10) Patent No.: US 7,070,797 B2
(45) Date of Patent: Jul. 4, 2006

(54) METHOD OF TREATING HEMATOLOGIC TUMORS AND CANCERS

(75) Inventors: Arthur B. Pardee, Cambridge, MA (US); Kenneth Anderson, Wellesley, MA (US); Deepak Gupta, Westborough, MA (US); Chiang Li, West Roxbury, MA (US); Youzhi Li, Dedham, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 277 days.

(21) Appl. No.: 10/209,388

(22) Filed: Jul. 31, 2002

(65) Prior Publication Data

US 2003/0036515 A1 Feb. 20, 2003

Related U.S. Application Data

(63) Continuation-in-part of application No. 10/007,352, filed on Nov. 7, 2001, now abandoned.

(60) Provisional application No. 60/246,552, filed on Nov. 7, 2000.

(51) Int. Cl.
*A61F 13/00* (2006.01)

(52) U.S. Cl. .................. 424/422; 424/400; 514/772.4; 514/773; 514/776; 514/781

(58) Field of Classification Search ................ 424/400, 424/422; 514/772.4
See application file for complete search history.

(56) References Cited

U.S. PATENT DOCUMENTS

| 5,424,073 | A | 6/1995 | Rahman et al. |
| 5,440,056 | A | 8/1995 | Klein et al. |
| 5,760,072 | A | 6/1998 | De Bont et al. |
| 5,763,625 | A | 6/1998 | Boothman et al. |
| 5,773,461 | A | 6/1998 | Wittman et al. |
| 5,807,888 | A | 9/1998 | Pandey et al. |
| 5,824,700 | A | 10/1998 | Frydman et al. |

(Continued)

FOREIGN PATENT DOCUMENTS

WO    WO 94/04145    3/1994

(Continued)

OTHER PUBLICATIONS

Li et al, Potent Inhibition of tumor survival in vivo by Beta lapachone plus taxol: Combining drugs imposes different artificial checkpoints, Nov. 9, 1999, PNAS, vol. 96, No. 23, pp. 13369-13374.*

(Continued)

*Primary Examiner*—Thurman K. Page
*Assistant Examiner*—David Vanik
(74) *Attorney, Agent, or Firm*—Mintz, Levin, Cohn, Ferris, Glovsky & Popeo, P.C.; Ivor R. Elrifi; Matthew Pavao

(57) ABSTRACT

Multiple myeloma and other hematologic tumors and/or malignancies can be treated by administration of a G1 and/or S phase drug, which is preferably β-lapachone, or a derivative or analog thereof, combined with a G2/M phase drug such as a taxane derivative, which is advantageously paclitaxel. This combination of the G1 and/or S phase drug with the G2/M phase drug results in an unexpectedly greater than additive (i.e., synergistic) apoptosis in multiple myeloma cells. The invention includes methods of treating multiple myeloma by administering the combination of the G1 and/or S phase drug and the G2/M phase drug, pharmaceutical compositions comprising the combination of drugs used in these methods, as well as pharmaceutical kits.

51 Claims, 11 Drawing Sheets

U.S. PATENT DOCUMENTS

| | | | |
|---|---|---|---|
| 5,969,163 A | 10/1999 | Frydman et al. | |
| 6,245,807 B1 | 6/2001 | Pardee et al. | |

FOREIGN PATENT DOCUMENTS

| | | |
|---|---|---|
| WO | WO 96/33988 | 10/1996 |
| WO | WO 97/08162 | 3/1997 |
| WO | WO 97/31936 | 9/1997 |
| WO | WO0731936 * | 9/1997 |
| WO | WO 00/61142 | 10/2000 |
| WO | WO0061142 * | 10/2000 |

OTHER PUBLICATIONS

Li et al, Potent Induction of Apoptosis by Beta-Lapachone in Human Multiple Myeloma Cell Lines and patient Cells, Dec. 6, 2000, Molecular medicine, vol. 6, No. 12, pp. 1008-1015.*

Li et al, Potent Inhibition of tumor survival in vivo by Beta lapachone plus taxol: Combining drugs imposes different artificial checkpoints, Nov. 9, 1999, PNAS, vol. 96, No. 23, pp. 13369-13374.*

Li, et al. (1995). *Cancer Res. 55*: 3712-3715.

Li, et al. (1999). *Proc. Natl. Acad. Sci. USA 96*(23): 13369-74.

Li (1999). *Mol. Med. 5*: 232-239.

Schaffner-Sabba, et al. (1984). *J. Med. Chem. 27*: 990-4.

Li, et al. (1993). *J. Biol. Chem. 268*(30): 22463-8.

Goncalves, et al. (1998). *Mol. and Biochem Parasitology 1*: 167-76. (1998).

Longo (1998). *Harrison's Principles of Internal Medicine* 14th edition: 713. (McGraw-Hill, New York).

Case, et al. (1977). *Am. J. Med. 63*: 897-903.

Otsuki, et al. (2000). *Cancer Res. 60*: 1.

Hooker (1936). *J. Am. Chem. Soc. 58*: 1181-1190.

Goncalves de Lima, et al. (1962). *Rev. Inst. Antibiot. Univ. Recife. 4*: 3-17.

Li, et al. (1993). *Proc. Natl. Acad. Sci. USA 90*: 1839-1842.

Schuerch and Wehrli (1978). *Eur. J. Biochem. 84*: 197-205.

Boorstein, et al. (1984). *Biochem. Biophys. Res. Commun. 118*(3): 828-834.

Boothman, et al. (1989). *Cancer Res. 49*: 605-612.

Tu, et al. (1996). *Blood 88*(5): 1805-1812.

Bloem and Lockhorst (1999). *Pathol. Bio. (Paris) 47*: 216-220.

Elledge (1996). *Science 274*: 1664-1672.

Hartwell and Kastan (1994). *Science 266*: 1821-1828.

Nurse (1997). *Cell 91*: 865-867.

Tang, et al. (2000). *Science 287*: 640-642.

Kingston, et al. (1986). "New Trends in Natural Products Chemistry" *Studies in Organic Chem. 26*: 219-235.

Mosmann (1983). *J. Immunol. Methods 65*: 55-63.

Treon, et al. (1998). *Blood 92*: 1749-1757.

Portela, et al. (1996). *Biochem Pharm 51*: 275-283.

Maruyama, et al. (1977). *Chem Lett* 847-850.

Sun, et al. (1998). *Tetrahedron Lett 39*: 8221-8224.

Gupta, et al. (1978). *Indian Journal of Chemistry 16B*: 35-37.

Gupta, et al. (1977). *Curr Sci 46*: 337.

DiChenna, et al. (2001). *J Med Chem 44*: 2486-2489.

Reme, et al. (2001). *Br J Haematol 114*: 406.

Suzuki, et al. (1992). *Eur J Immunol 22*: 1989.

Gado, et al. (2001). *Haematologica 86*: 227.

Dallas, et al. (1999) *Blood 93*: 1697.

Manning, et al. (1995). *Immunol Cell Biol. 73*: 326.

Takura, et al. (1996). *Cancer Res 26*: 2564.

Potter, et al. (1985). *J Exp Med 161*: 996.

Yaccoby, et al. (1998). *Blood 92*: 2908.

Urashima, et al. (1997). *Blood 90*: 754.

Frank, et al. (1976). *Am J Pathol 83*: 367.

Donaubauer, et al. (1998). *Regul Toxicol Pharmacol 27*: 189.

Uekama and Otagirl. (1987). *Crit Rev Ther Drug Carrier Syst 3*: 1.

Medline Online Database XP002241805 (NLM7641180) (1995) (*See*, Planchon et al. (1995) *Cancer Res 55* (17): 3706-3711).

Zhang et al. (1998). *Leukemia 12*(9): 1383-1391.

Gazitt et al. (1998). *International Journal of Oncology 13*(4): 839-848.

Li et al. (2000). *Mol. Med. 6*(12): 1008-1015.

* cited by examiner

A: ARH-77 
B: DOX-40 
C: mm.As 
D: mm.1R

A: ARH-77

B: ARH-77

3-bromo-β-lapachone
(MW 321)
(CO-502)

4-hydroxy-β-lapachone
(MW 258)
(CO-503)

4-acetoxy-β-lapachone
(MW 300)
(CO-504)

4-keto-β-lapachone
(MW 256)
(CO-505)

Dunnione Analog
(MW 242)
(CO-506)

4-hexanoyl-1,2-naphthoquinone
(MW 272)
(CO-507)

3-hydroxy-β-lapachone
(MW 258)

3-(3-methyl-2-butenyl)-4-methyl-β-lapachone

2-ethyl-6-hydroxynaptho[2,3-b]-furan-4,5-dione

METHOD OF TREATING HEMATOLOGIC TUMORS AND CANCERS

RELATED APPLICATION

This application is a continuation-in-part of U.S. Ser. No. 10/007,352, filed Nov. 7, 2001; now abandoned and claims priority to U.S. Ser. No. 60/246,552 filed Nov. 7, 2000, each of which is incorporated by reference in its entirety.

BACKGROUND OF THE INVENTION

Multiple myeloma ("MM") represents a malignant proliferation of plasma cells derived from a single clone. The terms multiple myeloma and myeloma are used interchangeably to refer to the same condition. The myeloma tumor, its products, and the host response to it result in a number of organ dysfunctions and symptoms of bone pain or fracture, renal failure, susceptibility to infection, anemia, hypocalcemia, and occasionally clotting abnormalities, neurologic symptoms and vascular manifestations of hyperviscosity. See D. Longo, in Harrison's Principles of Internal Medicine 14th Edition, p. 713 (McGraw-Hill, New York, 1998). Human multiple myeloma remains an incurable hematological malignancy that affects 14,400 new individuals in the United States annually (See Anderson, K. et al., Introduction. *Seminars in Oncology* 26:1 (1999)). No effective long-term treatment currently exists for MM. It is a malignant disease of plasma cells, manifested as hyperproteinemia, anemia, renal dysfunction, bone lesions, and immunodeficiency. MM is difficult to diagnose early because there may be no symptoms in the early stage. The disease has a progressive course with a median duration of survival of six months when no treatment is given. Systematic chemotherapy is the main treatment, and the current median of survival with chemotherapy is about three years, however fewer than 5% live longer than 10 years (See Anderson, K. et al., *Annual Meeting Report* 1999. Recent Advances in the Biology and Treatment of Multiple Myeloma (1999)).

While multiple myeloma is considered to be a drug-sensitive disease, almost all patients with MM who initially respond to chemotherapy eventually relapse (See Anderson, K. et al., *Annual Meeting Report* 1999. Recent Advances in the Biology and Treatment of Multiple Myeloma (1999)). Since the introduction of melphalan and prednisone therapy for MM, numerous multi-drug chemotherapies including Vinca alkaloid, anthracycline, and nitrosourea-based treatment have been tested (See Case, D C et al., (1977) *Am. J. Med* 63:897–903), but there has still been little improvement in outcome over the past three decades (See Case, D C et al., (1977) *Am. J. Med* 63:897–903; Otsuki, T. et al, (2000) *Cancer Res.* 60:1). Thus, the reversal of resistance to chemotherapeutic agents is an important area of research. New methods of treatment such as chemotherapy drugs or combinations are therefore urgently needed for treatment of MM.

The present inventors previously discovered that β-lapachone, when combined with Taxol® (paclitaxel; Bristol-Myers Squibb Co., N.Y., N.Y.) at moderate doses, has effective anti-tumor activity in a human ovarian, prostate and breast cancer xenograft models in nude mice. No signs of toxicity to the mice were observed, and no weight loss was recorded during the subsequent two months following treatment during which the tumors did not reappear (See Li, C J et al. (1999) *Proc. Natl. Acad. Sci. USA* 96:13369–13374). However, such conditions are different from MM and the current modes of treatment differ as well.

β-lapachone (3,4-dihydro-2,2-dimethyl-2H-naphtho [1,2-b] pyran-5,6-dione), a simple non-water soluble orthonapthoquinone, was first isolated in 1882 by Patemo from the heartwood of the lapacho tree (See Hooker, S C, (1936) *I. Am. Chem. Soc.* 58:1181–1190; Goncalves de Lima, O, et al., (1962) *Rev. Inst. Antibiot. Univ. Recife.* 4:3–17). The structure of β-lapachone was established by Hooker in 1896 and it was first synthesized by Fieser in 1927 (Hooker, S C, (1936) *I. Am. Chem. Soc.* 58:1181–1190). β-lapachone can be obtained by simple sulfuric acid treatment of the naturally occurring lapachol, which is readily isolated from *Tabebuia avellenedae* growing mainly in Brazil, or is easily synthesized from seeds of lomatia growing in Australia (Li, C J, et al., (1993) *J. Biol. Chem.* 268:22463–33464).

β-lapachone has been shown to have a variety of pharmacological effects. Numerous derivatives have been synthesized and tested as anti-viral and anti-parasitic agents, and it has been shown to have anti-trypanosomal effects (See Goncalves, A M et al. (1980) *Mol. Biochem. Parasitology* 1:167–176; Schaffner-Sabba, K. et al. (1984) *J. Med. Chem.* 27:990–994; Li, C J et al., (1993) *Proc. Natl. Acad. Sci. USA* 90:1839–1842). β-lapachone significantly prolongs the survival of mice infected with Rauscher leukemia virus, probably through inhibition of reverse transcriptase (Schaffner-Sabba, K. et al. (1984) *J. Med. Chem.* 27:990–994; Schuerch, A R et al., (1978 *Eur. J Biochem.* 84:197–205). The present inventors have demonstrated that β-lapachone inhibits viral replication and gene expression directed by the long terminal repeat (LTR) of the human immunodeficiency virus type I (Li, C J et al., (1993) *Proc. Natl. Acad. Sci. USA* 90:1839–1842).

β-lapachone was investigated as a novel and potent DNA repair inhibitor that sensitizes cells to ionizing radiation and DNA damaging agents (Boorstein, R J et al., (1984) *Biochem Biophys. Res. Commun.* 118:828–834; Boothman, et al., (1989) *Cancer Res.* 49:605–612). The present inventors have reported that β-lapachone and its derivatives inhibit eukaryotic topoisomerase I through a different mechanism than does camptothecin, which may be mediated by a direct interaction of β-lapachone with topoisomerase I rather than stabilization of the cleavable complex (Li, C J et al., (1999) *J. Biol. Chem.* 268:22463–22468). The present inventors and others have reported that β-lapachone induces cell death in human prostate cancer cells (See Li, C J et al., I (1995) *Cancer Res.* 55:3712–3715). Furthermore, the present inventors found that β-lapachone induces necrosis in human breast cancer cells, and apoptosis in ovary, colon, and pancreatic cancer cells through induction of caspase (Li, YZ et al., (1999) *Molecular Medicine* 5:232–239).

SUMMARY OF THE INVENTION

Multiple checkpoints are built into the machinery of the cell proliferation cycle where cells make a commitment to repair DNA damage or to undergo cell death. Unlike normal cells, cancer cells have lost checkpoint control and have an uncontrolled proliferation drive. The approximately $10^{16}$ cell multiplications in the human lifetime, together with inevitable errors in DNA replication and exposure to ultraviolet rays and mutagens, underscores the requirement for checkpoint functions. Major checkpoints occur at G1/S phase and at the G2/M phase transitions where cells make a commitment to repair DNA or undergo apoptosis. Cells are generally thought to undergo apoptosis when DNA damage is irreparable (Li, C J et al. (1999) *Proc. Natl. Acad. Sci. USA*

96:13369–13374). Identification of therapeutic agents modulating the checkpoint control may improve cancer treatment.

The present inventors have now discovered that β-lapachone is effective in treating individuals with MM and other hematologic tumors or malignancies. For example, β-lapachone suppresses cell survival and proliferation by triggering typical apoptosis in MM cells. Induction of cell death by β-lapachone has been demonstrated to be associated with cell cycle delays at the G1 and/or S phase, unlike most DNA damaging agents which arrest cells at the G2/M transition. This artificially imposed G1/S checkpoint delay by β-lapachone precedes p53-independent (Li, C J et al. (1999) *Proc. Natl. Acad. Sci. USA* 96:13369–13374) apoptotic or necrotic cell death in a variety of human carcinoma cells in vitro. Both apoptotic and necrotic cell death induced by β-lapachone are preceded by a rapid release of cytochrome c, followed by activation of caspase-3 in apoptotic cell death, but not in necrotic cell death (Li, YZ et al., (1999) *Molecular Medicine* 5:232–239). Importantly, the apoptotic effect of β-lapachone was observed in drug sensitive cells such as ARH-77, H S Sultan and MM.1S, and freshly derived MM cells from patients, as well as in MM cell lines MM.1 R, DOX.40, and MR.20, which are resistant to radiation, doxorubicin, and mitoxantrone, respectively. Apoptosis was not detected in normal peripheral blood mononuclear cells (PBMCs). β-lapachone-induced apoptosis in MM cells was preceded by a rapid release of cytochrome c, followed by the activation of caspase and poly (ADP ribose) polymerase (PARP) cleavage. The sensitivity to β-lapachone was not affected by expression of Bcl-2, a key mediator of drug resistance in myeloma cells (Tu, Y. et al., (1996) *Blood* 88:1805–12; Bloem, A. et al., (1999) *Pathol Bio (Paris)* 47: 216–220). Exogenous interleukin-6 (IL-6), important anti-apoptotic factor for MM cells (16), did not dampen the apoptotic effect of β-lapachone. These findings, therefore, show that β-lapachone is also a promising drug for treating human multiple myeloma.

In one embodiment, the present invention relates to a method for treating human multiple mycloma by administering a G1 and/or S phase drug, which is advantageously β-lapachone, or a derivative or analog thereof, in a therapeutically effective amount.

In another embodiment, a combination of a G2/M phase drug including, but not limited to, a taxane, its derivatives and analogs, and a G1 and/or S phase drug, preferably, but not limited to β-lapachone, or a derivative or analog thereof, can be administered for the treatment of MM and other hematologic tumors and/or malignancies.

In addition to treating multiple myeloma, β-lapachone, as well as the combination of β-lapachone, or a derivative or analog thereof, combined with a G2/M phase drug, may be used to treat other hematologic tumors and/or malignancies, such as childhood leukemia and lymphomas, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

A list of representative compounds is described in Table 1, infra. The combination of the present invention is particularly advantageous in the treatment of patients who have multiple myeloma. The method of the present invention comprises administering to the patient, in combination, an effective amount of a G1 and/or an S phase drug, in combination with a G2/M drug. Preferably, the combination is (1) a topoisomerase I inhibitor such as β-lapachone or its derivatives or analog thereof (G1 and/or S phase drug) and (2) a taxane, its derivatives or analogs thereof (G2/M drug), and pharmaceutically acceptable salts thereof.

As used herein, the phrase "taxane" or "taxane derivative" means any taxane which is or may be used in cancer chemotherapy due to its anti-neoplastic properties. Taxol® is a preferred taxane derivative.

As further used herein, the phrase "β-lapachone" refers to 3,4-dihydro-2,2-dimethyl-2H-naphtho [1,2-b] pyran-5,6-dione and derivatives and analogs thereof, and has the chemical structure:

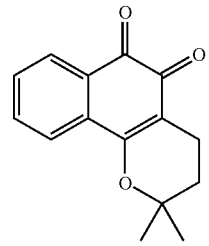

Preferred Derivatives and Analogs are Discussed Below.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

DETAILED DESCRIPTION OF THE INVENTION

Figure 1:
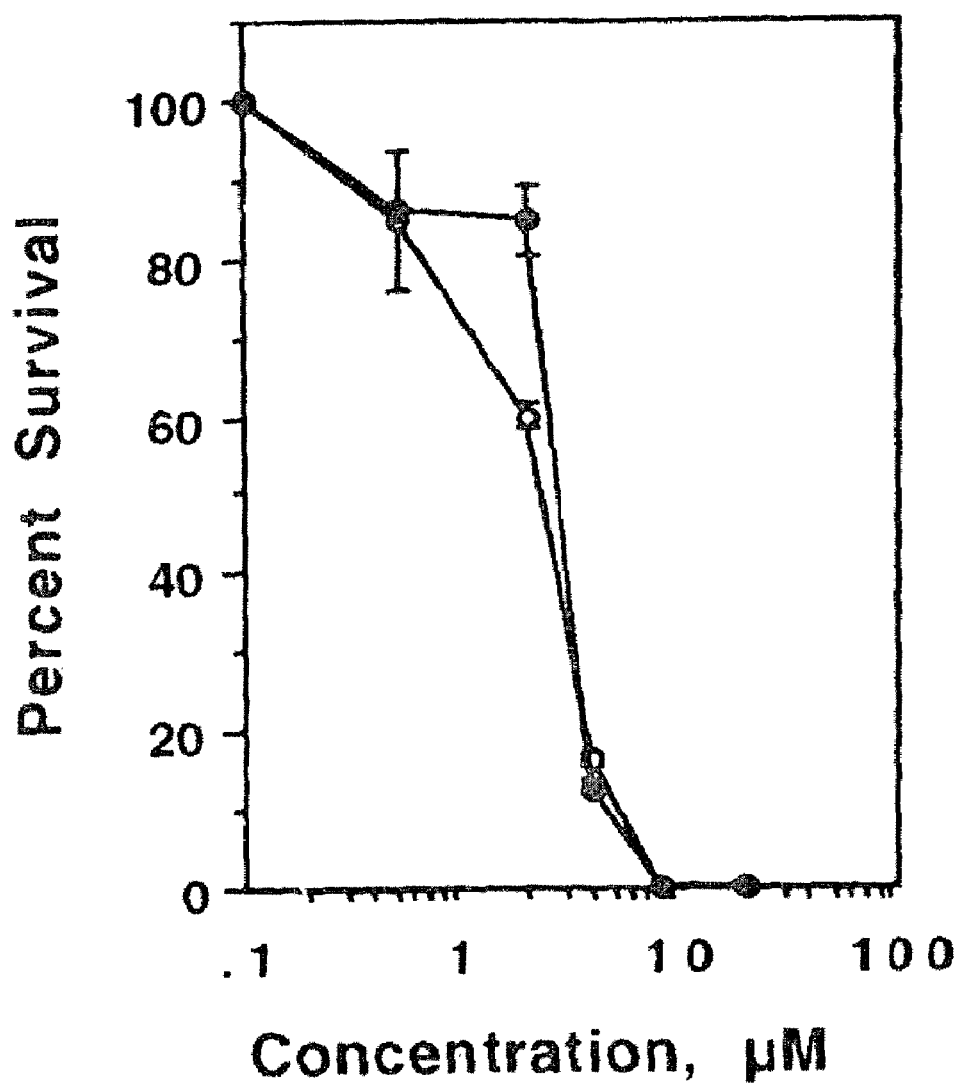
FIG. 1 illustrates the inhibition of colony formation (cell survival) by β-lapachone in human MM cells. (ARH-77 (○); Dox.40.(●)).

This invention provides for treating individuals afflicted with MM and other hematologic tumors and/or malignancies. This method comprises administering to an individual afflicted with MM an effective amount of a G1 and/or S phase drug, such as β-lapachone or a derivative or analog thereof. In another embodiment, the method comprises administering a combination therapy for treating multiple myeloma and other hematologic tumors and/or malignancies using methods which employ the administration of a G1 and/or S phase drug with a G2/M phase drug.

In one embodiment, the invention is directed to a method for treating a subject having malignant cells or inhibiting further growth of such malignant cells by administering a drug or compound that targets such cells at G1 and/or S phase checkpoints in the cell cycle. A second drug or compound that acts at the G2/M checkpoints in the cell cycle is then administered simultaneously with or following the G1 and/or S phase drug or compound. Individual compounds satisfying these criteria are known to those of ordinary skill in the art. For example, β-lapachone and its derivatives are G1 and S phase drugs. Whereas Taxol® and its derivatives are G2/M drugs. A list of representative compounds is set forth below in Table 1:

TABLE 1

| Type | Category | Compound Name | Chemical Formula |
|---|---|---|---|
| 1. | G1 and/or S phase drug | β-lapachone | 3,4-dihydro-2,2-dimethyl-2H-naphtho[1,2-b]pyran-5,6-dione |
| 2. | G1 phase drugs | Reduced β-lapachone | [1s[1α(R*), 3α7β,8β S*,4s*),8αβ]]-Methylbutanoic acid 1,2,3,7,8,8a-hexahydro-3,7-dimethyl-8-[2-(tetrahydor-4-hydroxy-6-0x0-2H-pyran-2-yl)ethyl[-1-naphthalenyl ester |
|  |  | Lovastatin |  |
|  |  | Mimosine | α-Amino-3-hydroxy-4oxo-1(4H)-pyridine propanoic acid |
|  |  | Tamoxifen | [Z]-2-[4-(1,2-Diphenyl-1-butenyl)-phenoxyl-N,N-dimethylethanamine |
| 3. | S phase drugs | Gemcitabine | 2',2'difluorodeoxycytidine |
|  |  | 5-FU | 5-fluorouracil |
|  |  | MTX | Methotrexate; N-[4[[(2,4-Diamino-6-pteridinyl)methyl]methylamino]benzoyl]-L-glutamic acid |
| 4. | G2/M drugs |  |  |
|  | (i) Microtubule-targeting | Taxol | 5-beta,20-epoxy-1,2-alpha,4,7,-beta,10-beta,13-alpha-hexahydroxy-tax-11-en-9-one 4,10-diacetate 2-benzoate 13-ester with (2R,3S)-N-benzoyl-3-phenyl-isoserine |
|  |  | Docetaxel | N-debenzoyl-N-tert-butoxycarbonyl-10-deacetyl taxol |
|  |  | Epothilone | Epithilone Polyketides A, B, C or D (desoxy-epothilone) |
|  |  | Vincristin | 22-Oxovincaleukoblastine |
|  |  | Vinbliastin | Vincaleukoblastine |
|  |  | Navelbine | Vinorelbine |
|  | (ii) Topoisomerase Poisons | Teniposide | VM-26; [5R-5α,5αβ,8aα,9β(R*)]]-5,8,8a,9-tetrahydro-5-(4-hydroxy-3,5-dimethoxyphenyl)-9-[[4,6-O-(2-thienylmethylene)-β-D-glucopyranosyl]oxy]furo[3',4':a6,7]naphtho[2,3-d]-1,3-dioxol-6(5aH)-one |
|  |  | Etoposide | VP-16; 4'-Demethylepipodophyllotoxin ethylidene-B-D-glucoside |
|  |  | Adriamycin | Doxorubicin; 14-Hydroxydaunomycin |
|  |  | Camptothecin | Cerubidin; Leukaemomycin C; Rubidomycin; Rubomycin C |
|  |  | Danunorubicin |  |
|  |  | Dactinomycin | Actactinomycin A IV; Actinomycin Cl; Actinomycin-[threo-val-pro-sar-meval] |
|  |  | Mitoxantrone | Idamycin; 4-demethoxy-daunfubicin |
|  |  | Amsacrine |  |
|  |  | Epirubicin |  |
|  |  | Idarubicin |  |

The combinations of the present invention are particularly advantageous using β-lapachone and Taxol®, where synergistic results should be obtained. Molecular changes underlying cell cycle delay at multiple checkpoints, for example G1 and/or S phase and G2/M phase, can for example result in the synergistic induction of apoptosis in malignant cells. Although not wishing to be bound by theory, it is believed that the synergistic effect is mediated by inhibition of cdc2 kinases and upregulation of p21. p21 controls G1 and S phase checkpoints (Elledge, S. J. (1996) *Science* 274, 1664–1672), and is involved in the regulation of the G2/M checkpoint (Hartwell L. H. et al., M.B. (1994) *Science*, 266, 1821–1828). Cell cycle checkpoints are also regulated by cdc2 kinases and their inhibitors (Elledge, S. J. (1996) *Science* 274, 1664–1672 and Nurse, P. (1997) *Cell* 91, 865–867).

Preferably, the G1 and/or S phase compounds are administered prior to, or simultaneously with, compounds that target a cell at the G2/M phase checkpoint.

More preferably, the G1 and/or S phase compounds are administered prior to the compounds that target a cell at the G2/M checkpoint.

Preferred G1 and/or S phase checkpoint targeting compounds include G1 and/or S phase drugs (for example, β-lapachone), G1 phase drugs (for example, lovastatin, mimosine, tamoxifen, and the like) and S phase drugs (for example, gemcitabine, 5-FU, MTX, and the like). β-lapachone, its derivatives and analogs (Formula Ia) are most preferred.

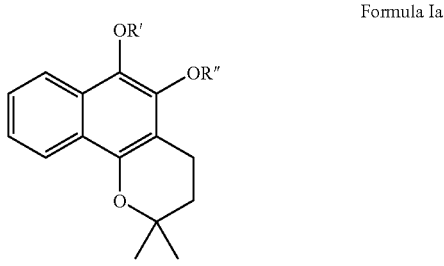

Formula Ia

Further, G1 and/or S phase checkpoint targeting drugs include derivatives of reduced β-lapachone. Preferred G2/M phase checkpoint targeting compounds include microtubule-targeting drugs (for example, Taxol®, docetaxel, vincristin, vinblastin, nocodazole, epothilones, navelbine, etc.) and topoisomerase poisons (for example, teniposide, etoposide, adriamycin, camptothecin, daunorubicin, dactinomycin, mitoxantrine, amsacrine, epirubicin, idarubicin, etc.).

Epothilones (epothilone polyketides) are microtubule-targeting drugs which stabilize microtubules by means of the same mechanisms as taxol (See Litang, et al. (2000) *Science* 287, 640–642). The epothilones are advantageous as they are effective against taxol-resistant tumors and are sufficiently water-soluble. Epothilones A and B are the most abundant in nature and 12,13-desoxy-epothilone B (epothilone D) has the highest therapeutic index. Epothilones (A, B, C, D or mixtures thereof) can be used in combination with β-lapachone and this could result in a synergistic induction of apoptosis in malignant cells which is similar to the combination of β-lapachone and Taxol®, as described earlier. For the purpose of this invention, epothilone would refer to epothilones A, B, C or D (desoxy-epothilone).

Preferred combinations include:

β-lapachone with Taxol®; β-lapachone with docetaxel; β-lapachone with vincristin; β-lapachone with vinblastin; β-lapachone with nocodazole; β-lapachone with teniposide; β-lapachone with etoposide; β-lapachone with adriamycin; β-lapachone with epothilone; β-lapachone with navelbine; β-lapachone with camptothecin; β-lapachone with daunonibicin; β-lapachone with dactinomycin; β-lapachone with mitoxantrone; β-lapachone with amsacrine; β-lapachone with epirubicin; or β-lapachone with idarubicin.

Reduced β-lapachone with Taxol®; reduced β-lapachone with docetaxel; reduced β-lapachone with vincristin; reduced β-lapachone with vinblastin; reduced β-lapachone with nocodazole; reduced β-lapachone with teniposide; reduced β-lapachone with etoposide; reduced β-lapachone with adriamycin; reduced β-lapachone with epothilone; reduced β-lapachone with navelbine; reduced β-lapachone with camptothecin; reduced β-lapachone with daunorubicin; reduced β-lapachone with dactinomycin; reduced β-lapachone with mitoxantrone; reduced β-lapachone with amsacrine; reduced β-lapachone with epirubicin; or reduced β-lapachone with idarubicin.

Lovastatin with Taxol®; lovastatin with docetaxel; lovastatin with vincristin; lovastatin with vinblastin; lovastatin with nocodazole; lovastatin with teniposide; lovastatin with etoposide; lovastatin with adriamycin; lovastatin with epothilone; lovastatin with navelbine; lovastatin with camptothecin; lovastatin with daunorubicin; lovastatin with dactinomycin; lovastatin with mitoxantrone; lovastatin with amsacrine; lovastatin with epirubicin; or lovastatin with idarubicin.

Mimosine with Taxol®; mimosine with docetaxel; mimosine with vincristin; mimosine with vinblastin; mimosine with nocodazole; mimosine with teniposide; mimosine with etoposide; mimosine with adriamycin; mimosine with epothilone; mimosine with navelbine; mimosine with camptothecin; mimosine with daunorubicin; mimosine with dactinomycin; mimosine with mitoxantrone; mimosine with amsacrine; mimosine with epirubicin; or mimosine with idarubicin.

Tamoxifen with Taxol®; tamoxifen with docetaxel; tamoxifen with vincristin; tamoxifen with vinblastin; tamoxifen with nocodazole; tamoxifen with teniposide; tamoxifen with etoposide; tamoxifen with adriamycin; tamoxifen with epothilone; tamoxifen with navelbine; tamoxifen with camptothecin; tamoxifen with daunorubicin; tamoxifen with dactinomycin; tamoxifen with mitoxantrone; tamoxifen with amsacrine; tamoxifen with epirubicin; or tamoxifen with idarubicin.

Gemcitabine with Taxol®; gemcitabine with docetaxel; gemcitabine with vincristin; gemcitabine with vinblastin; gemcitabine with nocodazole; gemcitabine with teniposide; gemcitabine with etoposide; gemcitabine with adriamycin; gemcitabine with epothilone; gemcitabine with navelbine; gemcitabine with camptothecin; gemcitabine with daunorubicin; gemcitabine with dactinomycin; gemcitabine with mitoxantrone; gemcitabine with amsacrine; gemcitabine with epirubicin; or gemcitabine with idarubicin.

5-FU with Taxol®; 5-FU with docetaxel; 5-FU with vincristin; 5-FU with vinblastin; 5-FU with nocodazole; 5-FU with teniposide; 5-FU with etoposide; 5-FU with adriamycin; 5-FU with epothilone; 5-FU with navelbine; 5-FU with camptothecin; 5-FU with daunorubicin; 5-FU with dactinomycin; 5-FU with mitoxantrone; 5-FU with amsacrine; 5-FU with epirubicin; or 5-FU with idarubicin.

MTX with Taxol®; MTX with docetaxel; MTX with vincristin; MTX with vinblastin; MTX with nocodazole; MTX with teniposide; MTX with etoposide; MTX with adriamycin; MTX with epothilone; MTX with navelbine; MTX with camptothecin; MTX with daunorubicin; MDC with dactinomycin; MDC with mitoxantrone; MTX with amsacrine; MTX with epirubicin; or MDC with idarubicin.

The combination of the present invention results in a surprising synergy which is beneficial in reducing tumor burden load and/or regressing tumor growth, especially in patients with metastatic disease.

Preferably, the human malignancy treated is multiple myeloma, although the invention is not limited in this respect, and other metastatic diseases may be treated by the combination of the present invention.

The individual components of the combination of the present invention will be addressed in more detail below.

As recited, one preferred component of the combination therapy described is a G2/M compound, which is preferably a taxane derivative. The taxanes are a family of terpenes, including, but not limited to paclitaxel and docetaxel (Taxotere®, Rhone-Poulenc Rorer, S. A., France), which were derived primarily from the Pacific yew tree (*Taxus brevifoilia*). *Taxus brevifoilia* has activity against certain tumors, particularly breast and ovarian tumors. Paclitaxel is a preferred taxane derivative in accordance with the present invention. Paclitaxel is considered to be an anti-microtubule agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions. The term "paclitaxel" includes both naturally derived and related forms and chemically synthesized compounds or derivatives thereof having anti-neoplastic properties including deoxygenated paclitaxel compounds such as those described in U.S. Pat. No. 5,440,056, incorporated herein by reference, and that is sold as TAXOL® by Bristol-Myers Squibb Co. Chemical formulas for paclitaxel are known and disclosed in U.S. Pat. No. 5,440,056. In addition to TAXOL®), other derivatives are well known, e.g., those mentioned in "Synthesis and Anticancer Activity of TAXOL® other Derivatives," D. G. I. Kingston et al., *Studies in Organic Chemistry*, vol. 26, entitled "New Trends in Natural Products Chemistry" (1986), Atta-ur-Rahman, P. W. le Queene, Eds. (Elvesier, Amsterdam 1986), pp. 219–235. Still other taxane derivatives are known in the art and include those, for example, as disclosed in U.S. Pat. Nos. 5,773,461; 5,760,072; 5,807,888; and 5,854,278, each of which is incorporated herein by reference.

The G2/M compound, such as the taxane derivative, may be administered in any manner found appropriate by a clinician in generally accepted efficacious dose ranges, such as those described in the *Physician Desk Reference*, 53rd Ed. (1999), Publisher Edward R. Barnhart, New Jersey ("PDR") for paclitaxel.

In general, the G2/M phase drug or compound, such as the taxane derivative, is administered intravenously at dosages from about 135 mg/m$^2$ to about 300 mg/m$^2$, preferably from about 135 mg/m$^2$ to about 175 mg/m$^2$, and most preferably about 175 mg/m$^2$. It is preferred that dosages be administered over a time period of about 1 to about 24 hours, and typically over a period of about 3 hours. Dosages can be repeated from 1 to about 4 weeks or more, preferably from about 2 to about 3 weeks.

As previously mentioned, the G2/M phase drug, such as the taxane derivative, will be administered in a similar regimen with a G1 and/or S phase drug, such as β-lapachone or a derivative or analog thereof, although the amounts will preferably be reduced from that normally administered. It is preferred, for example, that the taxane derivative be administered at the same time or after the β-lapachone has administered to the patient. When the taxane derivative is administered after the β-lapachone, the taxane derivative is advantageously administered about 24 hours after the β-lapachone has been administered.

The other component of the combination therapy for combination with the G2/M phase drug or compound is the G1 and/or S phase drug, which is preferably β-lapachone or a derivative or analog thereof.

β-lapachone (3,4-dihydro-2,2-dimethyl-2H-naphtho [1,2-b] pyran-5,6-dione) is a simple plant product with a chemical structure different from currently used anti-cancer drugs. It is obtained by sulfuric acid treatment of the naturally occurring lapachol, which is readily isolated from *Tabebuia avellanedae* growing mainly in Brazil. It can also be easily synthesized from lomatiol, isolated from seeds of lomatia growing in Australia (Hooker, S., et al., (1936) *J. Am. Chem. Soc.*, 58:1181–1190; Goncalves de Lima, 0., et al., (1962) *Rev. Inst. Antibiot. Univ. Recife.*, 4:3–17).

β-lapachone has been shown to have a variety of pharmacological effects. β-lapachone is a topoisomerase I inhibitor but acts by a different mechanism than camptothecin (Li, C. J., et al., (1993) *J. Biol. Chem.*, 268:22463–22468. Numerous β-lapachone derivatives have been synthesized and tested as anti-viral and anti-parasitic agent (Goncalves, A. M., et al., (1980) *Mol. Biochem. Parasitology*, 1:167–176; Schaffner-Sabba, K., et al., (1984) *J. Med. Chem.*, 27:990–994; Li, C., et al., (1993) *Proc. Nail. Acad. Sd. USA*, 90: 1842). β-lapachone and its derivatives, e.g. 3-allyl-β-lapachone, show anti-trypanosomal effects (Goncalves, A. M., et al., supra), the mechanism of which is at this time unclear. β-lapachone has also been shown to be a DNA repair inhibitor which sensitizes cells to DNA damaging agents (Boorstein, R. J., et al., (1984) *Biochem. Biophys. Res. Commun.*, 118:828–834; Boothman, D. A., et al., (1989) *J. Cancer Res.*, 49:605–612). β-lapachone is well tolerated in dogs, rats, mice, and chickens. The maximum tolerated dose, when given p.o. daily for one month, is 200 mg/kg in rats, and 100 mg/kg in dogs. Preferably, a compound such as β-lapachone or a derivative or analog thereof is administered to a patient in at least one dose in the range of 10 to 500,000 µg per kilogram body weight of recipient per day, more preferably in the range of 1000 to 50,000 µg per kilogram body weight per day, most preferably in the range of 5000 to 25,000 µg per kilogram body weight per day. The desired dose is suitably administered once or several more sub-doses administered at appropriate intervals throughout the day, or other appropriate schedule. These sub-doses may be administered as unit dosage forms, for example, containing 1 to 20,000 µg, preferably 10 to 10,000 µg per unit dosage form.

While β-lapachone is the preferred compound for use in the composition in accordance with the present invention, the invention is not limited in this respect, and β-lapachone derivatives or analogs, such as lapachol, and pharmaceutical compositions and formulations thereof are part of the present invention. Such β-lapachone analogs include those recited in PCT International Application PCT/US93/07878 (WO 94/04145), which is incorporated by reference herein in its entirety, and which discloses compounds of the formula:

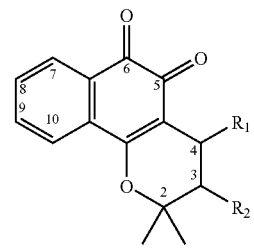

where R and $R_1$ are each independently hydrogen, substituted and unsubstituted aryl, substituted and unsubstituted alkenyl, substituted and unsubstituted alkyl and substituted or unsubstituted alkoxy. The alkyl groups preferably have from 1 to about 15 carbon atoms, more preferably from 1 to about 10 carbon atoms, still more preferably from 1 to about 6 carbon atoms. The term alkyl unless otherwise modified refers to both cyclic and noncyclic groups, although of course cyclic groups will comprise at least three carbon ring members. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The substituted R and $R_1$ groups may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms.

Other β-lapachone analogs contemplated in accordance with the present invention include those described in U.S. Pat. No. 6,245,807, which is incorporated by reference herein in its entirety, and which discloses β-lapachone analogs and derivatives having the structure:

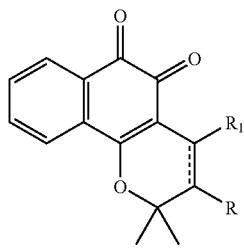

where R and $R_1$ are each independently selected from hydrogen, hydroxy, sulfhydryl, halogen, substituted alkyl, unsubstituted alkyl, substituted alkenyl, unsubstituted alkenyl, substituted aryl, unsubstituted aryl, substituted alkoxy, unsubstituted alkoxy, and salts thereof, where the dotted double bond between the ring carbons represents an optional ring double bond.

Additional β-lapachone analogs and derivatives are recited in PCT International Application PCT/US00/10169 (WO00/61142), which is incorporated by reference herein in its entirety, and which disclose compounds of the structure:

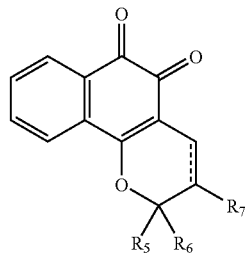

where $R_5$ and $R_6$ may be independently selected from hydroxy, $C_1$–$C_6$ alkyl, $C_1$–$C_6$ alkenyl, $C_1$–$C_6$ alkoxy, $C_1$–$C_6$ alkoxycarbonyl, —$(CH_2)_n$-phenyl; and $R_7$ is hydrogen, hydroxyl, $C_1$–$C_6$ alkyl, $C_1$–$C_6$ alkenyl, $C_1$–$C_6$ alkoxy, $C_1$–$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, wherein n is an integer from 0 to 10.

Other β-lapachone analogs and derivatives are disclosed in U.S. Pat. Nos. 5,763,625, 5,824,700, and 5,969,163, as well is in scientific journal articles, such as Sabba et al., *J Med Chem* 27:990–994 (1984), which discloses β-lapachone with substitutions at one or more of the following positions: 2-, 8- and/or 9-positions. See also Portela et al., *Biochem Pharm* 51:275–283 (1996) (substituents at the 2- and 9-positions); Maruyama et al., *Chem Lett* 847–850 (1977); Sun et al., *Tetrahedron Lett* 39:8221–8224 (1998); Goncalves et al., *Molecular and Biochemical Parasitology* 1:167–176 (1998) (substituents at the 2- and 3-positions); Gupta et al., *Indian Journal of Chemistry* 16B: 35–37 (1978); Gupta et al., *Curr Sci* 46:337 (1977) (substituents at the 3- and 4-positions); DiChenna et al., *J Med Chem* 44: 2486–2489 (2001) (monoarylamino derivatives). Each of the above-mentioned references are incorporated by reference herein in their entirety.

More preferably, analogs and derivatives contemplated by the present application are intended to encompass compounds having the general formula I and II:

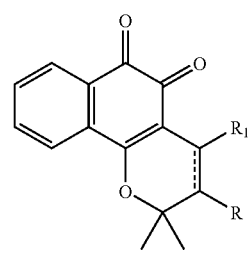

Formula I

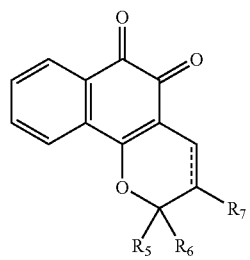

Formula II where the dotted double bond between the ring carbons represents an optional ring double bond and where R and $R_1$ are each independently selected from hydrogen, hydroxy, sulfhydryl, halogen, substituted alkyl, unsubstituted alkyl, substituted alkenyl, unsubstituted alkenyl, substituted aryl, unsubstituted aryl, substituted alkoxy, unsubstituted alkoxy, and salts thereof. The alkyl groups preferably have from 1 to about 15 carbon atoms, more preferably from 1 to about 10 carbon atoms, still more preferably from 1 to about 6 carbon atoms. The term alkyl refers to both cyclic and noncyclic groups. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The substituted R and $R_1$ groups may be substituted at one or more available positions by one or more suitable groups such as, for example, alkyl groups having from 1 to 10 carbon atoms or from 1 to 6 carbon atoms, alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms; and where $R_5$ and $R_6$ may be independently selected from hydroxy, $C_1$–$C_6$ alkyl, $C_1$–$C_6$ alkenyl, $C_1$–$C_6$ alkoxy, $C_1$–$C_6$ alkoxycarbonyl, —$(CH_2)_n$aryl, —$(CH_2)_n$-heteroaryl, —$(CH_2)_n$-heterocycle, or —$(CH_2)_n$-phenyl; and $R_7$ is hydrogen, hydroxyl, $C_1$–$C_6$ alkyl, $C_1$–$C_6$ alkenyl, $C_1$–$C_6$ alkoxy, $C_1$–$C_6$ alkoxycarbonyl, —$(CH_2)_n$-amino, —$(CH_2)_n$-aryl, —$(CH_2)_n$-heteroaryl, —$(CH_2)_n$-heterocycle, or —$(CH_2)_n$-phenyl, wherein n is an integer from 0 to 10.

Preferred analogs and derivatives also contemplated by the invention include compounds of the following general formula III:

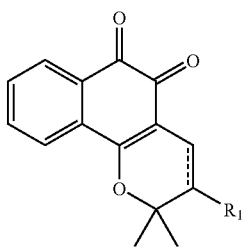

Formula III where $R_1$ is $(CH_2)_n$-$R_2$, where n is an integer from 0–10 and $R_2$ is hydrogen, an alkyl, an aryl a heteroaromatic, a heterocyclic, an aliphatic, an alkoxy, an allyloxy, a hydroxyl, an amine, a thiol, an amide, or a halogen.

Analogs and derivatives also contemplated by the invention include 4-acetoxy-β-lapachone, 4-acetoxy-3-bromo-β-lapachone, 4-keto-β-lapachone, 7-hydroxy-β-lapachone, 7-methoxy-β-lapachone, 8-hydroxy-β-lapachone, 8-methoxy-β-lapachone, 8-chloro-β-lapachone, 9-chloro-β-lapachone, 8-methyl-β-lapachone and 8,9-dimethoxy-β-lapachone.

Preferred analogs and derivatives also contemplated by the invention include compounds of the following general formula IV:

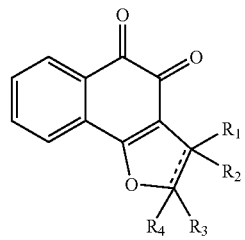

Formula IV where $R_1$–$R_4$ are each, independently, selected from the group consisting of H, $C_1$–$C_6$ alkyl, $C_1$–$C_6$ alkenyl, $C_1$–$C_6$ alkoxy, $C_1$–$C_6$ alkoxycarbonyl, —$(CH_2)_n$-aryl, —$(CH_2)_n$-heteroaryl, —$(CH_2)_n$-heterocycle, or —$(CH_2)_n$-phenyl; or $R_1$ and $R_2$ combined are a single substituent selected from the above group, and $R_3$ and $R_4$ combined are a single substituent selected from the above groups, in which case— is a double bond.

Preferred analogs and derivatives also contemplated by this invention include dunnione and 2-ethyl-6-hydroxynaphtho[2,3-b]-furan-4,5-dione.

Preferred analogs and derivatives also contemplated by the invention include compounds of the following general formula V:

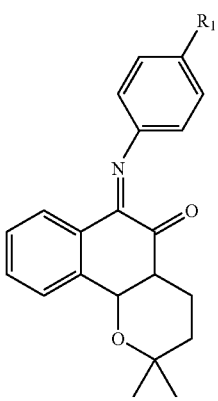

Formula V where $R_1$ is selected from H, $CH_3$, $OCH_3$ and $NO_2$.

Figure 11:
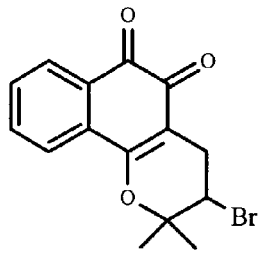
FIG. 11 illustrates preferred β-lapachone analogs and derivatives in accordance with the present invention.
Figure 11:
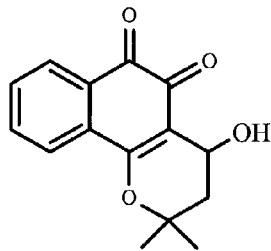
Figure 11:
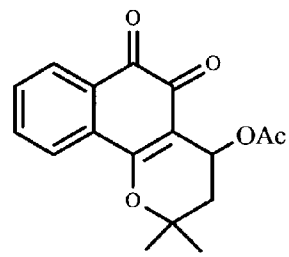
Figure 11:
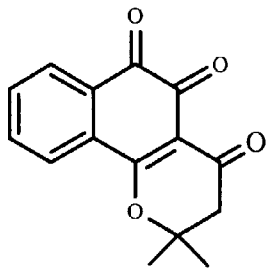
Figure 11:
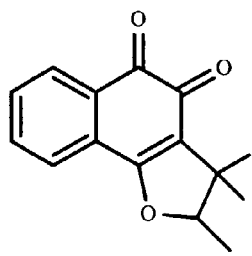
Figure 11:
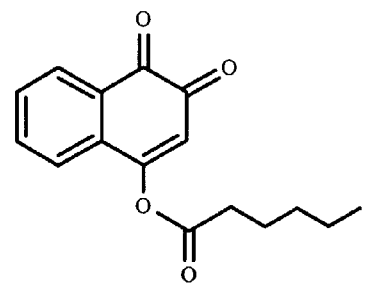
Figure 11:
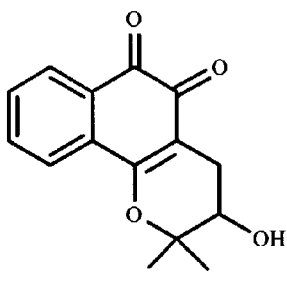
Figure 11:
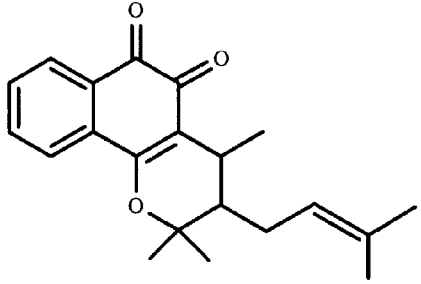
Figure 11:
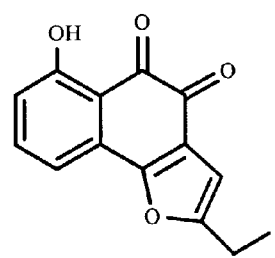

Preferred compounds of the above generic formulas are illustrated in FIG. 11.

As with the use of other chemotherapeutic drugs, the individual patient will be monitored in a manner deemed appropriate by the treating physician. Dosages can also be reduced if severe neutropenia or severe peripheral neuropathy occurs, or if a grade 2 or higher level of mucositis is observed, using the Common Toxicity Criteria of the National Cancer Institute.

The combination therapy agents described herein may be administered singly and sequentially, or in a cocktail or combination containing both agents or one of the agents with other therapeutic agents, including but not limited to, immunosuppressive agents, potentiators and side-effect relieving agents. As aforesaid, the therapeutic combination, if administered sequentially, is more effective when the β-lapachone component is administered prior to the taxane derivative. The therapeutic agents will preferably be administered intravenously or otherwise systemically by injection intramuscularly, subcutaneously, intrathecally or intraperitoneally.

The pharmaceutical compositions of this invention which are provided as part of the combination therapies may exist in the dosage form as a solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, nontoxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. A preferred carriers for the solubilization of β-lapachone is hydroxypropyl beta cyclodextrin, a water solubilizing carrier molecule. Other water-solubilizing agents for combining with β-lapachone and/or a taxane derivative, such as Poloxamer, Povidone K17, Povidone K12, Tween 80, ethanol, Cremophor/ethanol, polyethylene glycol 400, propylene glycol and Trappsol, are contemplated. Furthermore, the invention is not limited to water-solubilizing agents, and oil-based solubilizing agents such as lipiodol and peanut oil, may also be used.

In addition, the pharmaceutical composition or formulation may also include other carriers, adjuvants, or nontoxic, nontherapeutic, nonimmunogenic stabilizers and the like. Effective amounts of such diluent or carrier will be those amounts which are effective to obtain a pharmaceutically acceptable formulation in terms of solubility of components, or biological activity, and the like. Liposome formulations, are also contemplated by the present invention, and have been described See, e.g. U.S. Pat. No. 5,424,073, which is herein incorporated by reference.

For the purposes of the present invention, the G1 and/or S phase drugs or compounds, or derivatives or analogs thereof, and the G2/M drugs or compounds, or derivatives or analogs thereof, described herein include their pharmacologically acceptable salts, preferably sodium; analogs containing halogen substitutions, preferably chlorine or fluorine; analogs containing ammonium or substituted ammonium salts, preferably secondary or tertiary ammonium salts; analogs containing alkyl, alkenyl, aryl or their alkyl, alkenyl, aryl, halo, alkoxy, alkenyloxy substituted derivatives, preferably methyl, methoxy, ethoxy, or phenylacetate; and natural analogs such as naphthyl acetate. Further, the G1 and/or S phase compounds or derivatives or analogs thereof, and the G2/M phase compounds or derivatives or analogs thereof, described herein may be conjugated to a water-soluble polymer or may be derivatized with water-soluble chelating agents or radionuclides. Examples of water soluble polymers are, but not limited to: polyglutamic acid polymer, copolymers with polycaprolactone, polyglycolic acid, polyactic acid, polyacrylic acid, poly (2-hydroxyethyl 1 -glutamine), carboxymethyl dextran, hyaluronic acid, human serum albumin, polyalginic acid or a combination thereof. Examples of water-soluble chelating agents are, but not limited to: DIPA (diethylenetriaminepentaacetic acid), EDTA, DTTP, DOTA or their water-soluble salts, etc. Examples of radionuclides include, but not limited to: $^{111}$In, $^{90}$Y, $^{166}$Ho, $^{68}$Ga, $^{99m}$Tc, and the like.

Although intravenous administration is preferred as discussed above, the invention is not intended to be limited in this respect, and the compounds can be administered by any means known in the art. Such modes include oral, rectal, nasal, topical (including buccal and sublingual) or parenteral (including subcutaneous, intramuscular, intravenous and intradermal) administration.

For ease of administration and comfort to the patient, oral administration is generally preferred. However, oral administration typically requires the administration a higher dose than intravenous administration. Thus, depending upon the situation—the skilled artisan must determine which form of administration is best in a particular case—balancing dose needed versus the number of times per month administration is necessary.

In administering a G1 and/or S phase compound such as β-lapachone, the normal dose of such compound individually is utilized as set forth below. However, when combination therapies are used, it is preferable to use a lower dosage—typically 75% or less of the individual amount, more preferably 50% or less, still more preferably 40% or less.

In therapeutic applications, the dosages of the agents used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. An effective amount of a pharmaceutical agent is that which provides an objectively identifiable improvement as noted by the clinician or other qualified observer. Regression of a tumor in a patient is typically measured with reference to the diameter of a tumor. Decrease in the diameter of a tumor indicates regression. Regression is also indicated by failure of tumors to reoccur after treatment has stopped.

This invention further includes pharmaceutical combinations comprising a taxane derivative and a dose of β-lapachone or a derivative or analog thereof as provided above and kits for the treatment of cancer patients comprising a vial of the taxane derivative and a vial of β-lapachone or a derivative or analog thereof at the doses provided above. Preferably, the kit contains instructions describing their use in combination.

The invention is further defined by reference to the following examples. It is understood that the foregoing detailed description and the following examples are illustrative only and are not to be taken as limitations upon the scope of the invention. It will be apparent to those skilled in the art that many modifications, both to the materials and methods, may be practiced without departing from the purpose and interest of the invention. Further, all patents, patent applications and publications cited herein are incorporated herein by reference.

EXAMPLES

Example 1

Chemicals. β-lapachone was dissolved at 20 mM concentration in dimethyl sulfoxide (DMSO), aliquoted, and stored at −20° C. for cell culture use.

Cell Cultures. Cell lines used in this study were provided by the Department of Adult Oncology, Dana-Farber Cancer Institute, Boston, Mass. ARH-77, MM.1 S and HS sultan which are MM cell lines; mm.As are a MM patient's cells; MM.1R, DOX .40, and MR.20 are resistant to radiation, doxorubicin, and mitoxantrone, respectively. Cells were maintained at 37° C. in 5% $CO_2$, in 100% humidity, and were cultured in RPMI1640 medium (Life Technologies Inc.), supplemented with 10% FCS, 2 mM L-glutamine.

Colony Formation Assay. Exponentially growing cells were seeded at 2000 cells/well in six well plates and were allowed to attach for 48 h. Drugs were added directly in less than 5 μl of concentrated solution (corresponding to a final DMSO concentration of less than 0.1%). Control plates received the same volume of DMSO alone. After 24 h cells were rinsed and fresh medium was added. Cultures were observed daily for 10 to 20 days, and then were fixed and stained with modified Wright-Giemsa stain (Sigma). Colonies of greater than 30 cells were scored as survivors.

Cell Proliferation Assay. Cell Proliferation was determined by $^3$H-thymidine uptake assays and the 3[4,5-dimethylthiazol-2-yl]-2,5-diphenyltetrazolium bromide (Thiazolyl blue, MTT) assay (Sigma Co.). The conversion of the soluble yellow dye to the insoluble purple formazan by the mitochondrial dehydrogenase of viable cells was used for measurement of cell proliferation (Mosmann, T., (1983) *J. Immunol. Methods* 65:55–63). Briefly, cells were plated in a 96 well plate at 20,000 cells/well, cultured for 48 h in complete growth medium, then treated with β-lapachone for 24 h. MTT solution (5mg/mi) was added in ⅒th of culture volume to the culture medium, and after 3 to 4 hr the converted dye was solubilized with acidic isopropanol and optical density was read with an ELISA reader at a wavelength of 570 nm with a background subtraction at 630–690 nm (17). For the $^3$H-thymidine uptake assay, after drug treatment cells were pulsed with $^3$H-TdR (Dupont, Wilmington, Del.; 0.5 μCi/well) during the last 6 hours of 1-day cultures, harvested onto glass filters by use of a HARVESTAR 96 MACH II (Tomtec, Orange, Conn.) cell harvester, and counted on a 1205 Betaplate (Gaithersburg, Md.) scintillation counter (See Treon, S P et al., (1998) *Blood* 92:1749–57).

Apoptosis Assay. Apoptosis was determined by three independent assays. One determined the sub-G1 fraction by propidium iodide staining of nuclei as described previously (13, 19, 20, 22). The second measured the membrane changes determined by the externalization of phosphatidylserine (13, 21). Briefly, cells were treated with β-lapachone for 24 h, harvested, washed in PBS, resuspended in binding buffer, incubated with annexin V-FITC, and analyzed by flow cytometry. The third assay, by DNA laddering, was carried out as described (19,20,22).

Western blot analysis. Whole cell lysate and S-100 fraction were prepared from exponential growing cells. The ECL assay system was used to detect Bcl-2 levels and the cytochrome c released from mitochondria (S-100 fraction) and also PARP immunoblot analyses. Briefly, cell lysate protein samples were electrophoresed on a sodium dodecyl sulfate-polyacrylamide gel and then electrophoretically transferred to a nitrocellulose membrane. The blot was blocked, washed, and incubated with the Bcl-2 antibody (Oncogene Science) or using anti-PARP monoclonal antibody (Pharmingen, San Diego, Calif.) at 1:1000 dilution. The filter was then incubated with a second antibody that was conjugated with horseradish peroxidase. Finally, the filter was developed with detection reagents (RPN 2109; Amersham) and exposed to a hyperfilm-ECL (RPN 2103). The cytochrome c release was carried out as described (Li, YZ et al., (1999) *Molecular Medicine* 5:232–239).

Ablation of colonies in human MM cells by β-lapachone. To test the anti-survival effect of β-lapachone drug-sensitive human MM cell line ARH-77 and DOX-40 doxorubicin resistant cells were treated with β-lapachone in vitro. Cell survival was determined by colony formation assay. β-lapachone decreased cell survival in both cell lines with an IC100 of 4 μm (FIG. 1).

Figure 2:
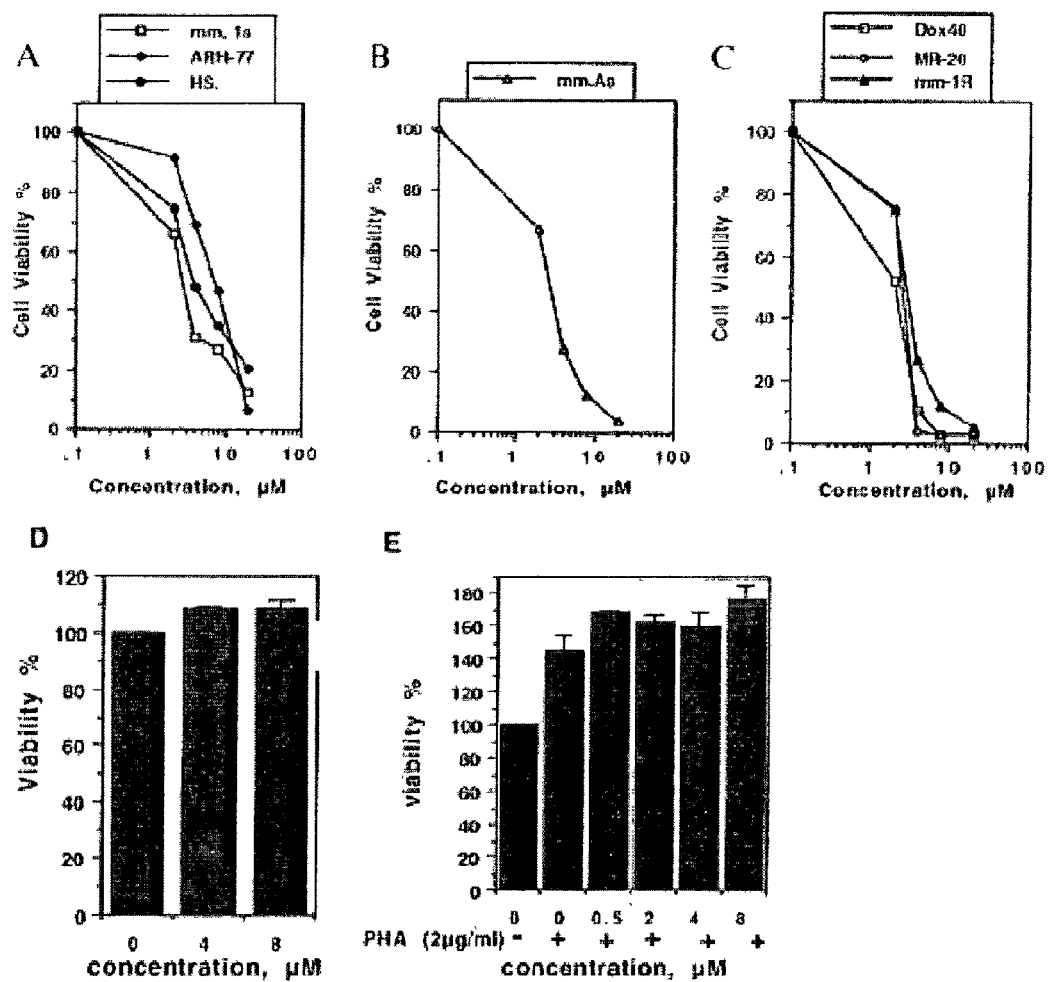
FIG. 2 illustrates the differential effect of β-lapachone on proliferation of MM cells versus normal PBMC. Proliferation of MM cells, quiescent PBMC, proliferative PBMC cultured in the absence of or at β-lapachone concentrations of (0.5, 2, 4, 8, or 20 μM for 24 hours was measured by MTT assay. Cells used include in (A) ARH-77, MM.1S and HS sultan (sensitive MM cell lines), in (B) mm.As (MM patient cell), in (C) MM.1R, DOX.40, and MR.20 (resistant cell lines), in (D) quiescent PBMC, in (E) proliferating PBMC (generated by 72 hours incubation with PHA at 2 μg/ml). In the absence of β-lapachone, cells were treated with an equal volume of DMSO.

Differential effect β-lapachone on proliferation of MM cells versus normal PBMC. To determine whether the differential inhibition of colony formation occurs through anti-proliferative activity, proliferation of MM cells cultured in the absence of or plus β-lapachone (2, 4, 8 and 20 μM) for 24 h was measured by MTT assay. At a concentration of 4 μM, the MTT in cultures were evaluated and found to be significantly decreased in all 7 MM cell lines (FIG. 2). There was a dramatic reduction in the proliferation of patient's MM cells (mm.As) and drug-resistant MM cells (mml.R, DOX-40, MR.20). No cross-resistance was observed. The same results could be seen by $^3$H-thymidine uptake assay.

To investigate the cytotoxicity of β-lapachone on human PBMC, the cells were isolated from anticoagulant-treated blood. Proliferative PBMC were generated by 72 hours incubation with phytohemagglutinin (PHA) at 2 μg/ml (Case, D C Jr. et al., (1977) *Am. J. Med.* 63:897–903). Growth of cells cultured in the absence or with β-lapachone (0.5, 2, 4 and 8 μM) for 24 hours was measured by MTT. Both fresh and proliferative PBMC growth was not decreased. No cytotoxicity was observed (FIG. 2), as compared to MM cells.

Figure 3:
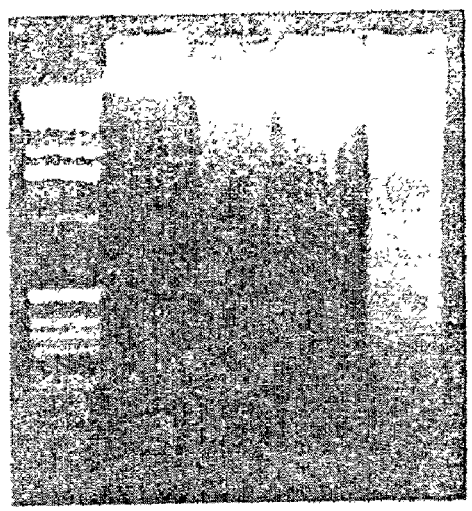
FIG. 3 illustrates induction of DNA fragmentation by β-lapachone in human MM cells. DNA laddering, a typical feature of apoptosis, was induced in (A): ARH-77 treated with β-lapachone (0, 2, 4, 8 μM); in (B): DOX-40; (C): mm.As; (D): mm.1R treated with β-lapachone. After exposure to the drug for 24 hours, genomic DNA was extracted and subjected to agarose gel electrophoresis.
Figure 3:
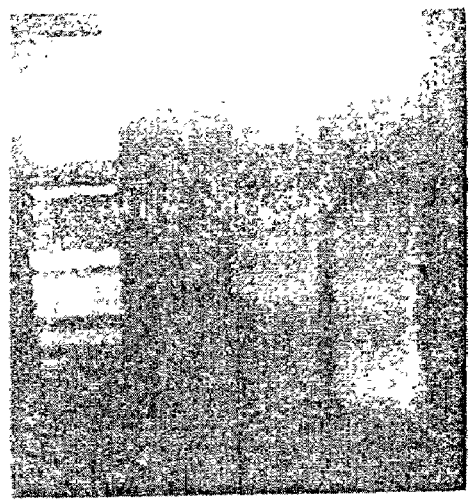
Figure 3:
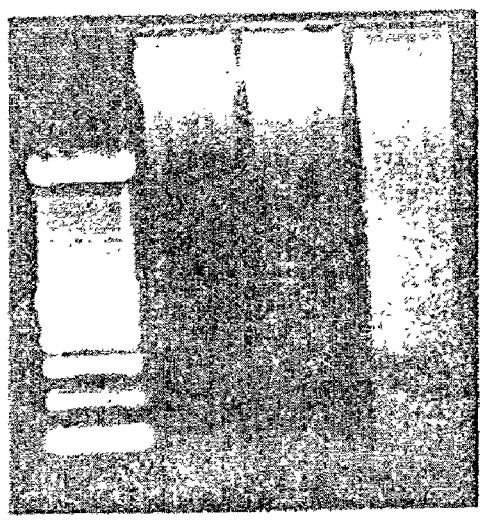
Figure 3:
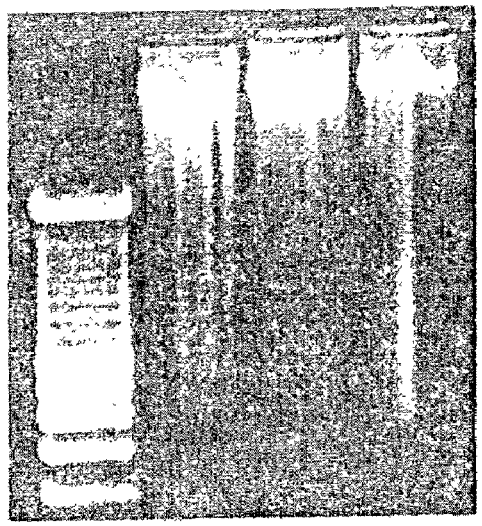
Figure 4:
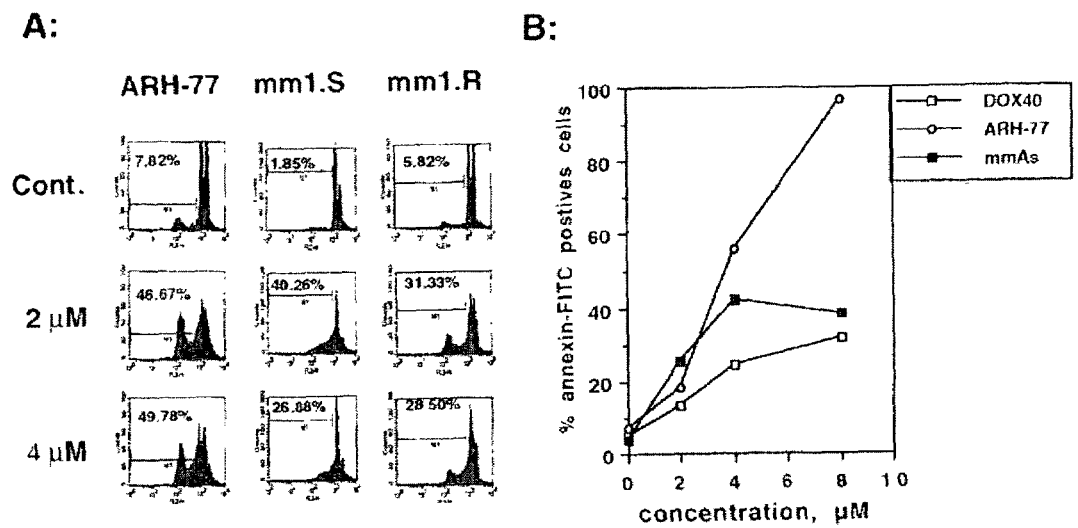
FIG. 4 illustrates induction of apoptosis by β-lapachone in human MM cells. Human ARH-77, mm.1S, and mm.1R cells were treated with B-lapachone, 0 μM (DMSO), 2 μm, or 4 μM, for 24 hours before they were subjected to flow cytometric analysis after staining with propidium iodide (P1) for quantitating the sub-G1 fraction (A), or for the analysis of externalization of phosphatidylserine (B), as measured by Annexin V staining. DOX-40 (□), ARH-77 (○), mm.As (■).

Induction of apoptosis by β-lapachone. To determine if the extensive cell death observed in proliferating human MM cells after treatment with β-lapachone is by apoptosis or necrosis, three independent assays were performed. First, at 24 h post drug exposure, cellular genomic DNA was subjected to gel electrophoresis. As shown in FIG. 3, β-lapachone induced a DNA laddering typical of apoptosis. Second, the PI staining procedure was used to determine the sub-GI fraction as a test for apoptosis. As shown in FIG. 4A, sub-G1 cells were detected. In the third assay, externalization of phosphatidylserine was determined, as measured by Annexin-V staining of these cells (FIG. 4B). The percentage of Annexin-V positive cells correlated with the sub-G1 fractions. All these results show that β-lapachone induced apoptotic death of these cells.

Figure 5:
FIG. 5 shows that apoptosis, induced by β-lapachone, is accompanied by mitochondrial cytochrome c release and PARP cleavage. In A, ARH-77 cells were treated with DMSO (lane 1) or β-lapachone at 4 μM for 0.5 hours (lane 2), 2 hours (lane 3), 4 hours (lane 4). Mitochondria cytochrome c release was determined by Western blot assay as described in Materials and Methods. In B, ARH-77 cells were treated with DMSO (lane 1) or β-lapachone at 2 μM for 2 hours (lane 2), 6 hours (lane 3), 12 hours (lane 4), 24 hours (lane 5), 48 hours (lane 6). An Immunoblot analysis of the lysates was performed with anti-PARP antibody.
Figure 5:
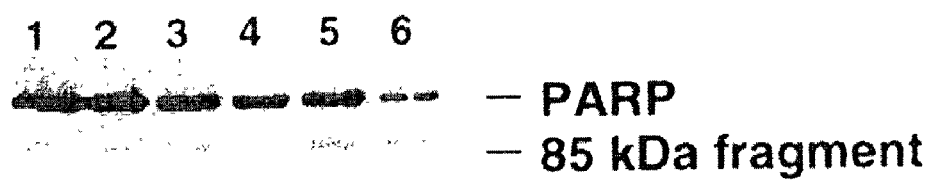

Apoptosis induced by β-lapachone is independent of expression of Bcl-2 and is preceded by cytochrome c release, and is followed by PARP cleavage. Expression of Bcl-2 has been implicated in the resistance of cancer cells including MM to chemotherapeutic drugs (14, 15). To determine if apoptosis in MM cells is due to lack or altered Bcl-2 expression, Bcl-2 was measured by Western blot assay. Bcl-2 was expressed in ARH.77 and mml.R cells and was not changed by β-lapachone, which does not correlate with their sensitivity to β-lapachone-induced apoptosis. Release of cytochrome c from mitochondria into cytosol has been implicated as an important step in apoptosis. To determine if β-lapachone triggers cytochrome c release, cells were analyzed for cytoplasmic cytochrome c at 2 h after drug treatment. As shown in FIG. 5A, cytochrome c was released into cytoplasm shortly after β-lapachone treatment when cells were fully viable by trypan blue exclusion and MTT assay, suggesting that cytochrome c release is an early event in β-lapachone induced apoptosis in MM cells. Next, β-lapachone was examined to determine if it induces PARP cleavage, a hallmark of apoptosis that indicates activation of caspase. As expected, two fragments corresponding to the remaining intact PARP protein (116 KDa) and the typical apoptotic 85 KDa fragment were visualized. (FIG. 5B).

Example 2

Chemicals. β-lapachone was synthesized and dissolved in 40% hydroxypropyl β-cyclodextrin at a concentration of 10 mg/mL and kept at room temperature in a dark container. Hydroxypropyl β-cyclodextrin was dissolved in distilled water at a concentration of 10 mg/mL and kept at room temperature. MATRIGEL®, a basement membrane matrix was purchased from Becton Dickinson Labware (BD Biosciences, Two Oak Park Drive, Bedford, Mass.) and was dissolved in Dulbecco's modified Eagle's medium with 50 µg/mL Gentamycin and kept frozen at −20° C. MATRIGEL® is extracted from the Engelbreth-Holm-Swarm mouse tumor, a tumor rich in extracellular matrix proteins. The major matrix components are laminin, collagen IV, entactin, and heparin sulfate proteoglycan (perlecan); the matrix also contains growth factors, matrix metalloproteinases (MMPs [collagenases]), and plasminogen activators, without any inhibitors of metalloproteinases (TIMPs). The MATRIGEL matrix is a solution at 4° C. and gels at room temperature to form a three-dimensional reconstituted basement membrane. This model system closely mimics the structure, composition, physical properties, and functional characteristics of the basement membrane in vivo and provides a physiologically relevant environment for studies of cell morphology, biochemical function, migration or invasion, and gene expression. The frozen MATRIGEL® matrix was thawed overnight at 4° C. before use.

Cell Cultures. RPMI 8226 cells (a human multiple myeloma cell line) were provided Dr. William Dalton (Lee Moffit Cancer Center, Tampa, Fla.). They were maintained by frequent passages in RPMI 1640 (Cellgro®, Mediatech Inc., Herndon, Va.) containing 10% Fetal Bovine serum (FBS) (GibcoBRL, Life Technologies, Grand Island, N.Y.) supplemented with $2 \times 10^{-3}$M L-Glutamine, 100 units/mL penicillin (Pen), and 100 µg/mL streptomycin (Cellgro®, Mediatech Inc., Herndon, Va.) in 162 cm² cell culture flasks (Costar®, Corning Incorporated, Corning, N.Y.). The exponentially growing cell lines were CD138+,CD38+/CD45RA−, EBV negative, and pathogen free.

Mice. Forty male 6-week-old Bg-Nu-Xid mice (deficient in T, B, and NK cells) were obtained from the FCRDC, Frederick, Bethesda, Md. and housed at the Redstone animal facility at DFCI. These mice have 3 separate mutations—Beige (Bg) autosomal recessive mutation associated with impaired chemotaxis and motility of macrophages & deficiency of NK cells; the nude (nu) autosomal recessive mutation associated with depletion of T cells due to thymic agenesis; and the X-linked immune defect (xid) which produces functional defects of B-lymphocytes. The animals were raised in a barrier facility in cages with sawdust bedding and laminar air at 19–22° C. Rodent food and sterile drinking water were supplied ad libitum. The mice were quarantined to rule out development of any disease. One mouse died during transport, and 5 others were lost because of dehydration (n=2), probable infection (n=2) and excessive bleeding due to trauma (n=1). After 1 week, enrofloxacin (a quinolone antibiotic) was added in drinking water of all mice. All procedures involving animals were approved by and performed according to guidelines of the Institutional Animal Care and Use Committee of the Dana Farber Cancer Institute (DFCI).

Histologic Analysis. The mice were sacrificed by cervical dislocation when the tumor reached 20 mm in their largest diameter or they became moribund, as per the policy of the Animal Protocol Committee at Dana Farber Cancer Institute. The mice were anesthetized with isoflurane, and retroorbital blood was collected. The tumors were dissected from the soft tissue (fascia, muscle, skin, etc.) and were fixed in 10% neutralized formalin. Liver, spleen, kidneys, lung, heart and brain from each group were also removed and fixed in formalin. The tissues were dehydrated and embedded in paraffin blocks. They were sectioned into slices 5 µm thick, stained with hematoxylin and eosin (HE), and examined by light microscopy for evidence of apoptosis.

Statistical Analysis. Statistical analysis was done using the student's 't' test for comparing the differences in tumor volumes and degree of apoptosis between β-lapachone and control groups. p value of <0.05 was considered significant.

Design. Thirty-four mice were included in the study. RPMI 8226 ($3 \times 10^7$) multiple myeloma cells were washed 3 times, re-suspended in 100 µL RPMI 1640, and injected subcutaneously in the right flank of all mice along with 100 µL of MATRIGEL® matrix using a hypodermic 27G needle and 1 mL syringe. The mice were observed for well-being and development of tumors daily, and were weighed weekly.

Figure 6:
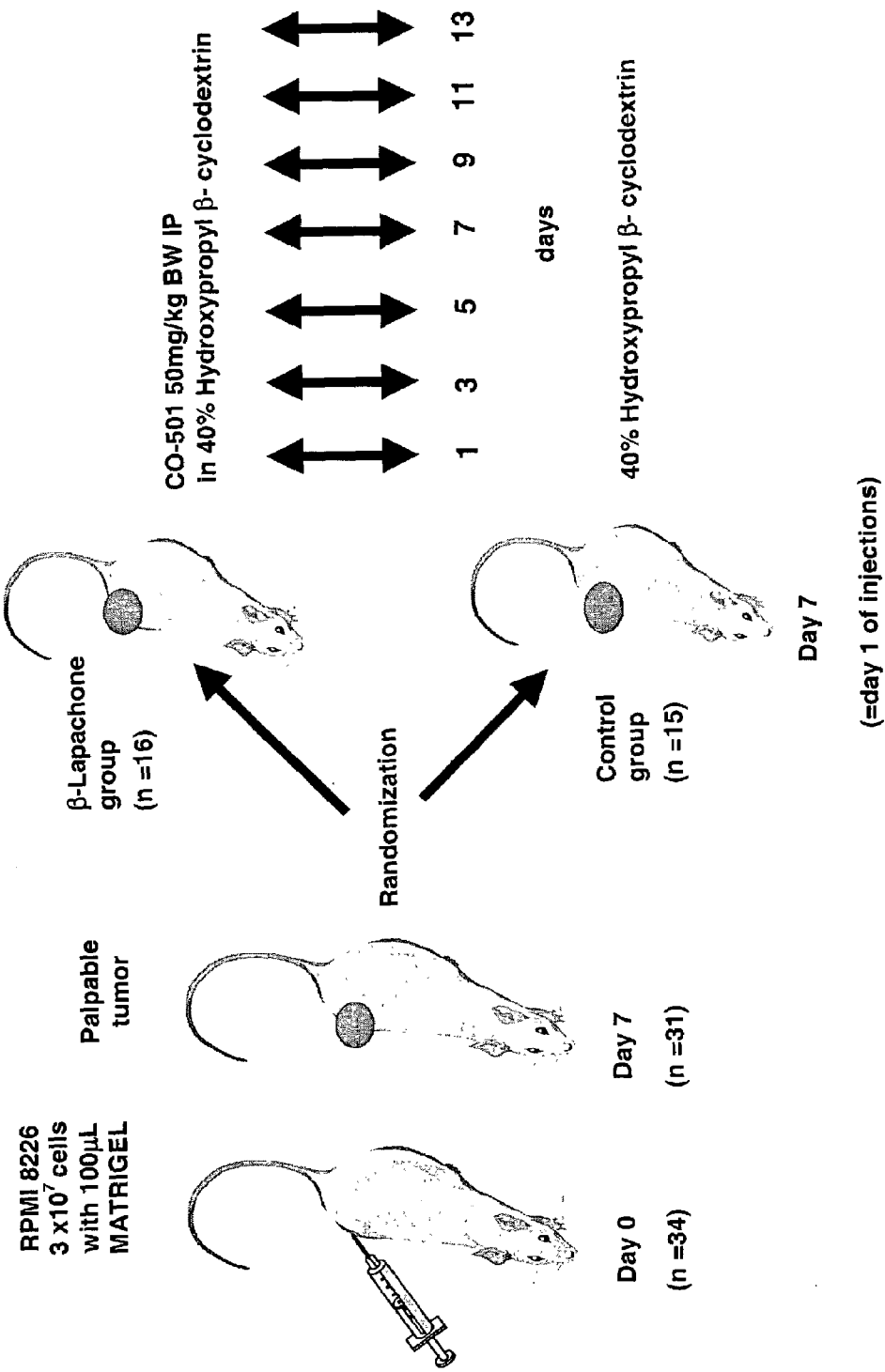
FIG. 6 is a schematic illustrating the injection of RPMI 8226 MM cells and the resulting tumor formation in Bg-Nu-Xid mice.

Localized palpable tumors developed in all mice (n=34) by a mean of 7 days after injection of RPMI 8226 cells. Once the tumors were palpable, they were measured by hand held vernier calipers in 2 orthogonal diameters every other day. Thirty-one mice were randomized to β-lapachone (n=16) and control (n=15) groups. The mice in the control group received 50 mg/kg body weight of 40% hydroxypropyl β-cyclodextrin solution intraperitoneally at the lower left abdominal area every other day. The mice in the β-lapachone group received β-lapachone in 40% hydroxypropyl β-cyclodextrin at 50 mg/kg body weight intraperitoneally every alternate day (FIG. 6). The usual volume at each injection was 125 µL. The diameters of the tumors were recorded, and the volumes were calculated using standard formula for cylindrical objects i.e. $0.523 \times (\text{Smaller diameter})^2 \times \text{Larger diameter}$. Mice were sacrificed when the tumor was ≧20mm in largest diameter or they became moribund.

This xenograft mouse model is attractive because it is easily established, allows monitoring growth of subcutaneous tumors by external measurements, and can be used to study the effects of various chemotherapeutic agents. Rapidly growing tumors may show some areas of apoptosis/necrosis, but is not a major obstacle in the evaluation of cytotoxicity of various novel potential therapeutic agents. Similar models have been reported previously using anti-gp130 agonist monoclonal antibodies (B1+I2) to study growth and immortalization of multiple myeloma patient cells (Reme et al. Br J Haematol 114:406, 2001) and using anti-human IL-6R antibody PM1 and anti human IL-6 antibody MH 166, to inhibit growth of IL-6 dependent cell line (S6B45) (Suzuki et al. Eur J Immunol 22:1989, 1992). Various animal models for testing multiple myeloma therapeutic agents have been reported previously (Gado et al. Haematologica 86: 227, 2001; Dallas et al. Blood 93:1697, 1999; Manning et al. Immunol Cell Biol 73:326, 1995; Takura et al. Cancer Res 26:2564, 1996; Potter et al. J Exp Med 161:996, 1985; Yaccoby et al. Blood 92:2908, 1998; Urashima et al. Blood 90:754, 1997). The Bu-Nu-Xid xenograft mouse model is relatively inexpensive, reproducible, homogeneous, and easy to generate; allows for ready external measurements; and provides for histopathological assessment of samples.

Figure 7:
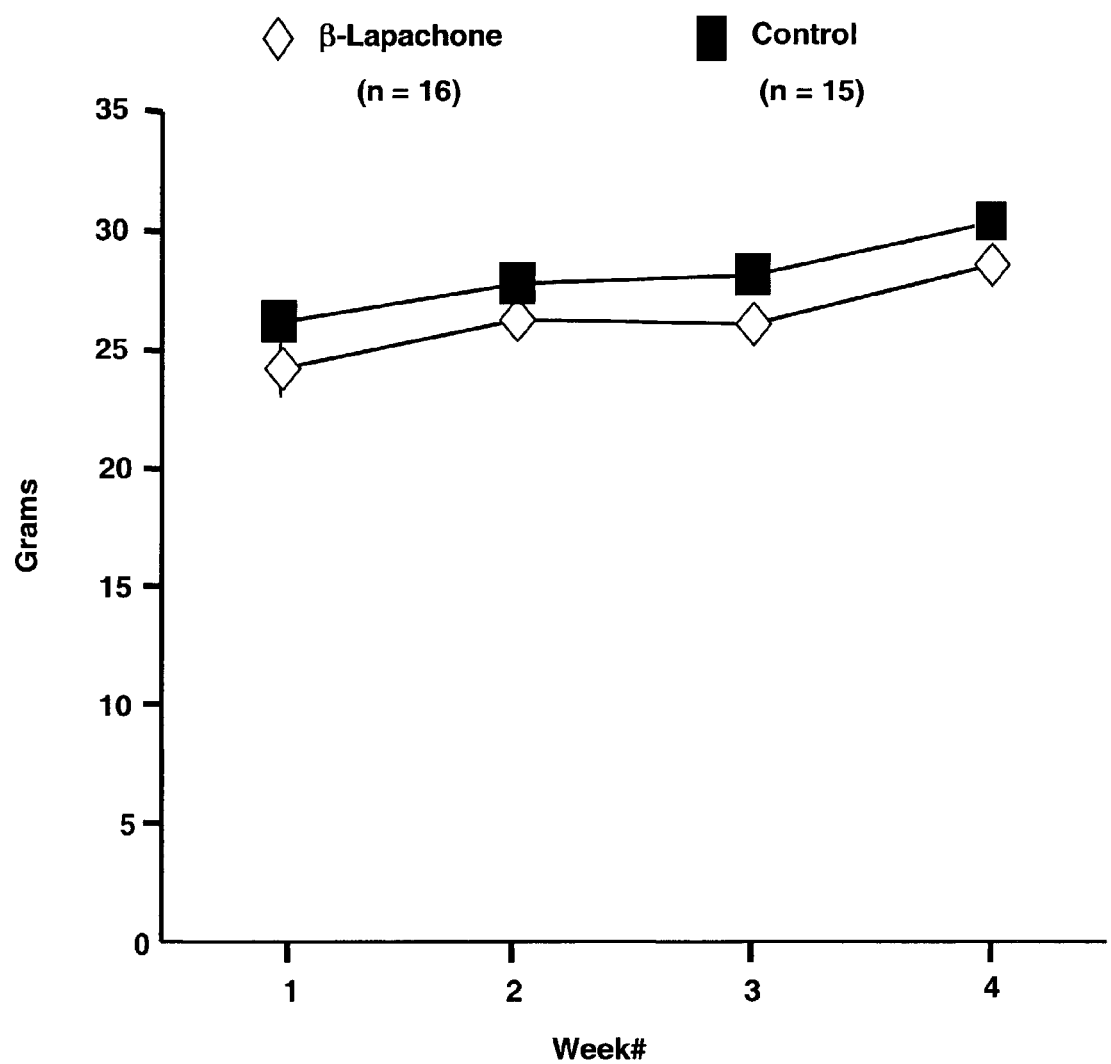
FIG. 7 is a graph showing the average weight pattern of mice during the study.

Determination of β-lapachone and cyclodextrin toxicity. Mice in both groups tolerated β-lapachone and hydroxypropyl β-cyclodextrin well. No mice died in either group and all gained weight (FIG. 7). There was no evidence of overt toxicity of β-lapachone or hydroxypropyl β-cyclodextrin in either cohort. One mouse developed iatrogenic intra-peritoneal hemorrhage after injection of β-lapachone which resolved in 36 h. Mild tubular vacuolization of kidneys was found in both β-lapachone and control groups. Since this effect was present in both groups, hydroxypropyl β-cyclodextrin is implicated, as has been previously reported (Frank et al. Am J Pathol 83:367, 1976) and these nephrotoxic changes are reversible with cessation of treatment (Donaubauer et al. Regul Toxicol Pharmacol 27:189, 1998). Furthermore, the toxicity of cyclodextrins has been reduced by developments of newer derivatives, which form complexes with a variety of drugs (Uekama and Otagiri, Crit Rev Ther Drug Carrier Syst 3:1, 1987).

Figure 8:
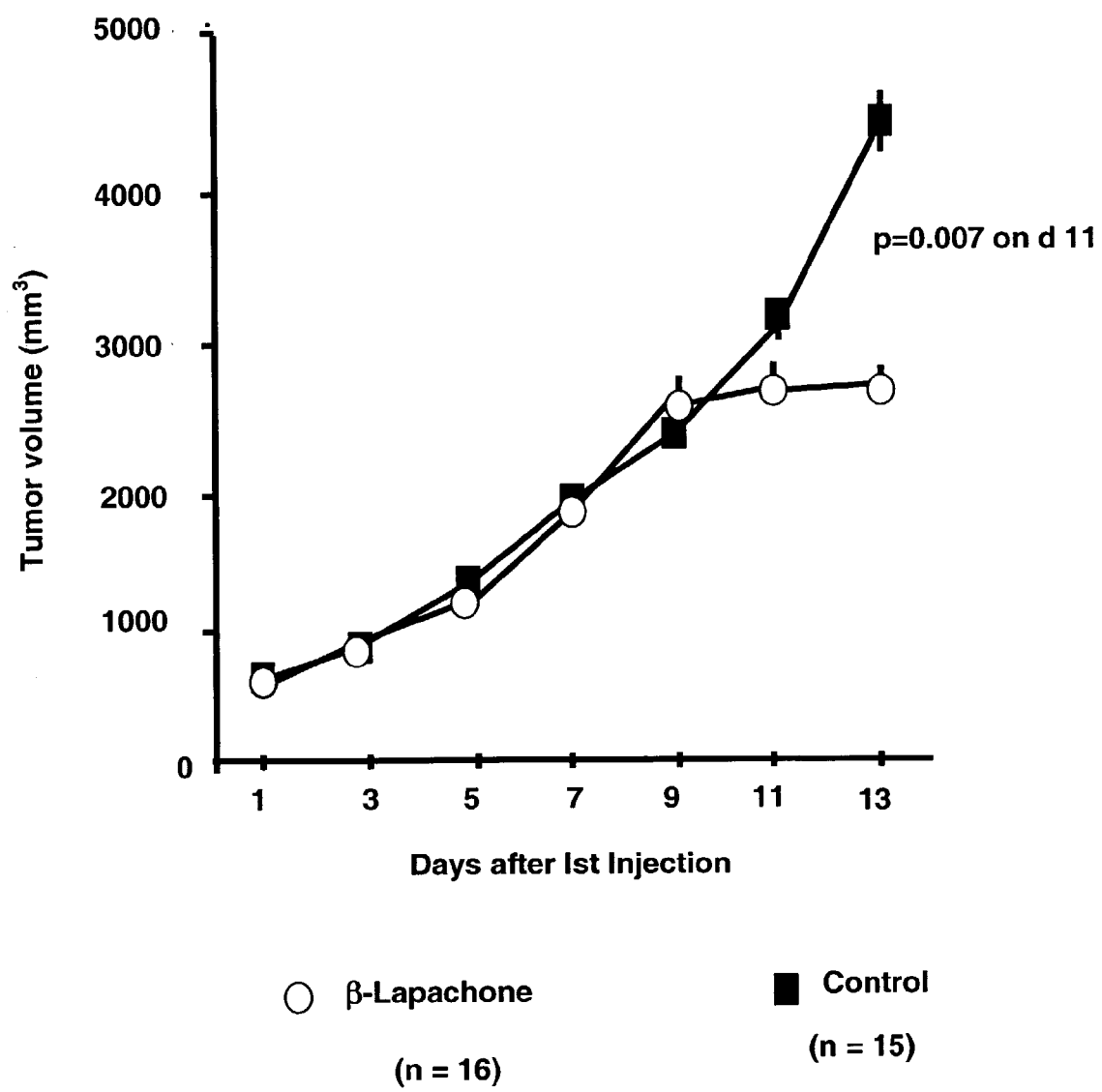
FIG. 8 is a graph showing the effect on β-lapachone/Hydroxypropyl β-cyclodextrin on tumor volume.
Figure 9:
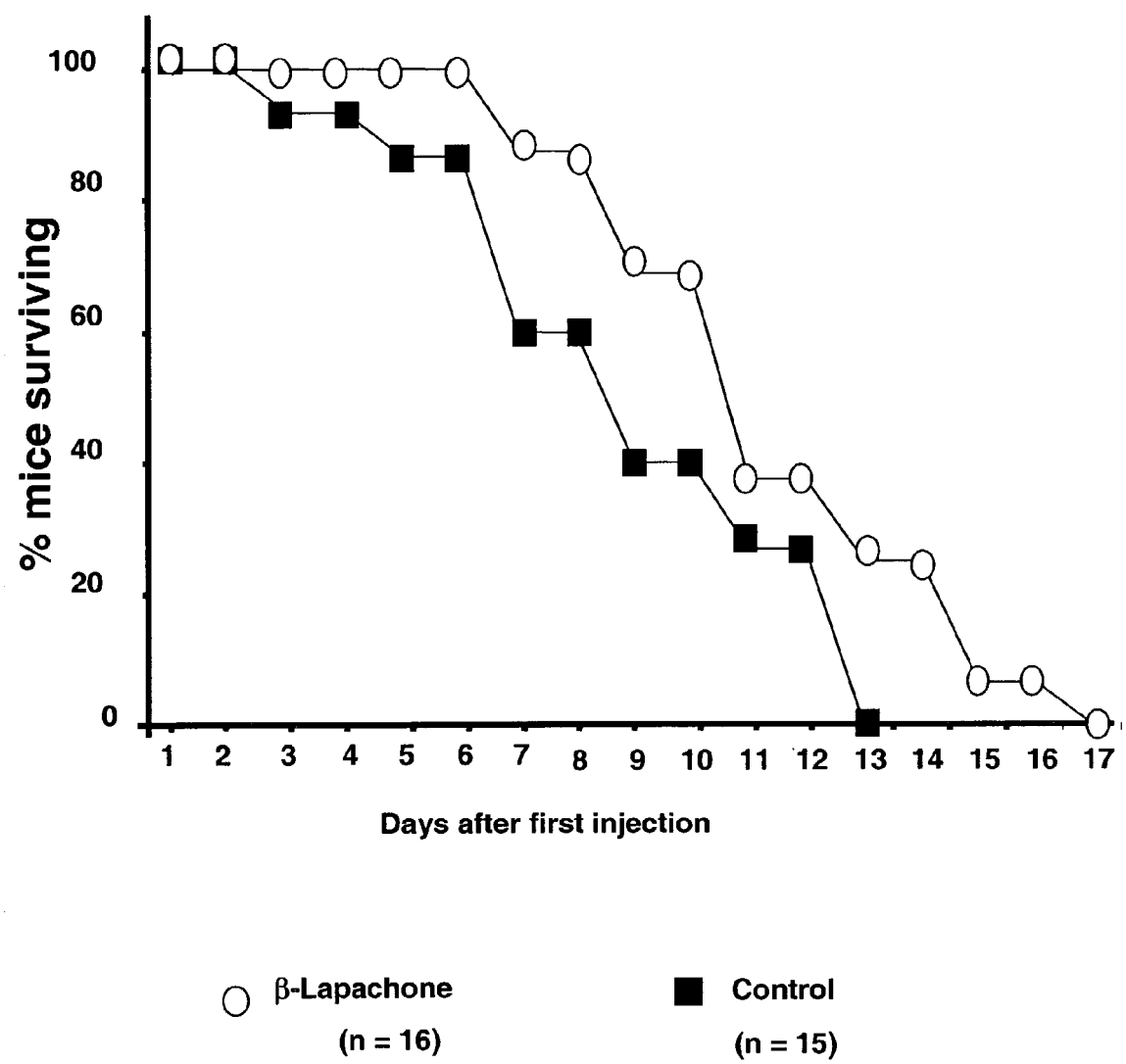
FIG. 9 is a graph showing the effect of β-lapachone/hydroxypropyl β-cyclodextrin on the survival of mice in both groups.

Effects of β-lapachone on tumor volume. Mice in control group received a maximum of 6 doses of hydroxypropyl β-cyclodextrin, whereas the mice in the β-lapachone group were able to receive a maximum of 8 doses of this agent. There was a statistically significant decrease in tumor volume of mice in β-lapachone group (p=0.007) versus control group (FIG. 8) by day 11. Importantly, survival was greater at day 5, 7, 9, 11, 13, 15 and 17 in the β-lapachone group compared to controls (FIG. 9), suggestive of slower in vivo tumor growth in β-lapachone group.

Histologic Staining. Histopathologic examination revealed that tumors were not encapsulated and were locally invasive to soft tissues, including muscle, without any distant metastasis. Tumors were vascularized by blood vessels of murine origin, with a minor variable degree (0–10%) of cell death primarily in their cores. Apoptosis was assessed histopathologically on the basis of (1) chromatin condensation and aggregation near the nuclear membrane with convolution of the nuclear membrane; (2) enlarged and abnormally granular nucleolus; (3) shrinkage and rounding of cells; (4) blebbing of cell membranes; and (5) minor dilation of endoplasmic reticulum and mitochondria. There was a statistically significant increase in MM cell apoptosis (p=0.001) in tumors in the β-lapachone (mean±SD=41.1%±12.7) versus control (mean±SD =20.0%±10.4) groups, as assessed by two blinded independent observers using light microscopy (FIG. 10A).

Figure 10:
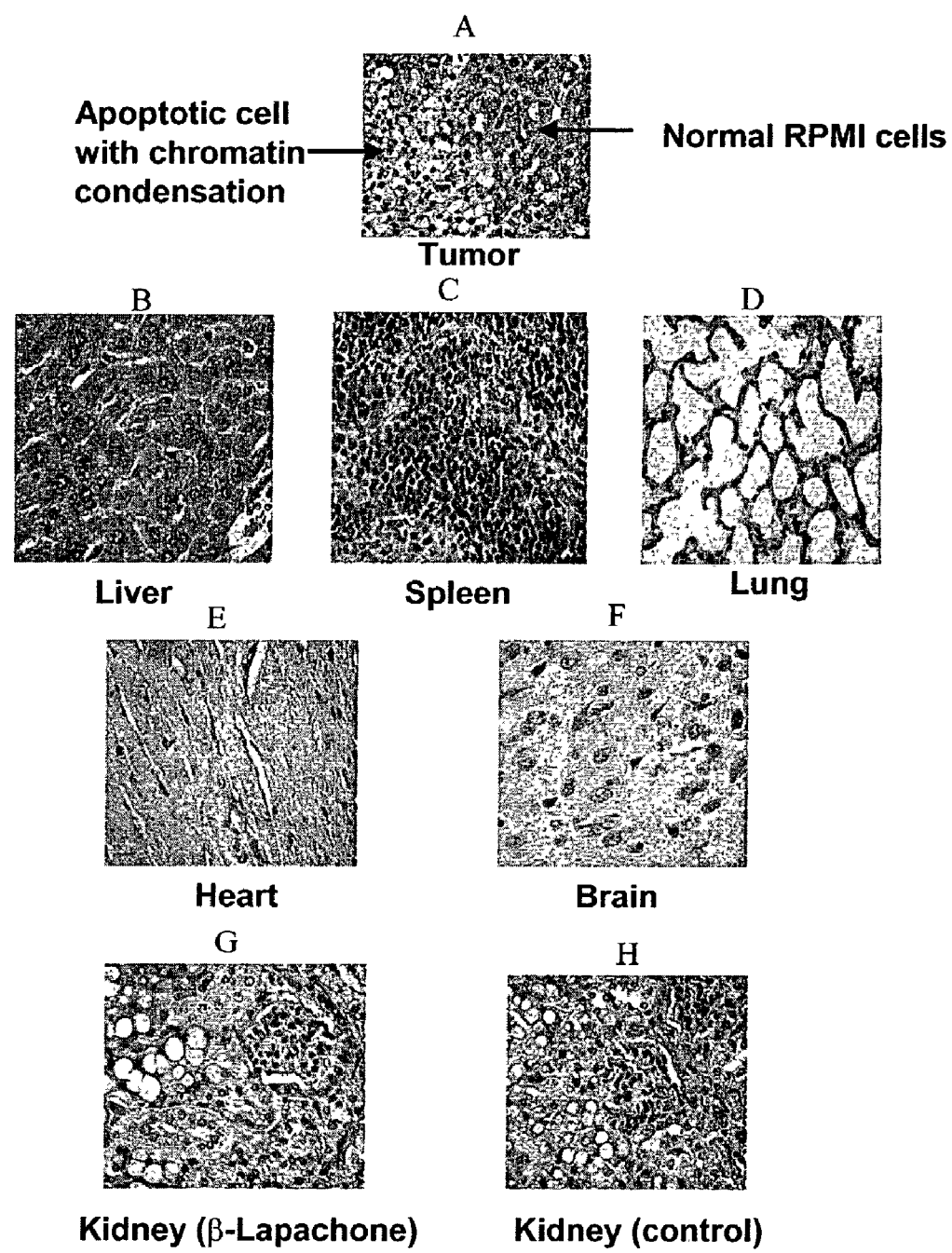
FIG. 10 is representative photomicrographs showing the effect of β-lapachone/hydroxypropyl β-cyclodextrin on tumors, as well as liver, spleen, lung, heart, brain and kidneys.

There was no microscopic evidence of any toxicity of β-lapachone or hydroxypropyl β-cyclodextrin on liver, heart, lung, brain, and spleen in mice in either β-lapachone or control groups (FIGS. 10B, C, D, E, F). Kidneys from mice in both groups showed mild tubular vacuolization, suggesting tubular toxicity of hydroxypropyl β-cyclodextrin (FIGS. 10G, H). The magnification for the photomicrographs was 400X.

These results indicate that β-lapachone is safe and effective at inhibiting tumor cell growth, associated with prolonged host survival in vivo. Thus it can be concluded that β-lapachone has significant anti-tumor activity with minimal toxicity and can be used to treat multiple myeloma in vivo.

Although the foregoing invention has been described in some detail by way of illustration and example for the purposes of clarity of understanding, one skilled in the art will easily ascertain that certain changes and modifications may be practiced without departing from the spirit and scope of the appended claims.

All references described herein are incorporated by reference.

What is claimed is:

1. A method of treating multiple myeloma in a subject, the method comprising administering to the subject a therapeutically effective amount of Beta-lapachone, or a derivative or analog thereof.

2. The method of claim 1, further comprising administering a therapeutically effective amount of a taxane derivative, or a derivative or analog thereof.

3. The method of claim 2, wherein the taxane derivative is paclitaxel.

4. The method of claim 2, wherein the Beta-lapachone or a derivative or analog thereof, and the taxane derivative or a derivative or analog thereof are administered intravenously.

5. The method of claim 2, wherein the tax ane derivative is administered simultaneously with the Beta-lapachone.

6. The method of claim 2, wherein the taxane derivative is administered following administration of the Beta-lapachone.

7. The method of claim 2, wherein the taxane derivative is administered within 24 hours after the Beta-lapachone is administered.

8. The method of claim 2, wherein the therapeutically effective amount of the Beta-lapachone, or a derivative or analog thereof, is contained in a first vial, and the taxane derivative, or a derivative or analog thereof, is contained in a second vial, the contents of the first and second vials being administered to the patient simultaneously or sequentially.

9. The method of claim 7, wherein the Beta-lapachone, or a derivative or analog thereof in the first vial is Beta-lapachone, and the taxane derivative in the second vial is paclitaxel.

10. The method of claim 2, wherein the taxane derivative is administered intravenously at a dosage from approximately 135 mg/m$^2$ to about 300 mg/m$^2$.

11. The method of claim 10, wherein the taxane derivative is administered intravenously at a dosage of approximately 175 mg/m$^2$.

12. The method of claims 1 or 2, wherein the Beta-lapachone, or a derivative or analog thereof, and the taxane derivative, or a derivative or analog thereof, further comprises a pharmaceutically acceptable carrier.

13. The method of claim 12, wherein the pharmaceutically acceptable carrier is a water solubilizing carrier molecule selected from the group consisting of Poloxamer, Povidone K17, Povidone K12, Tween 80, ethanol, Cremophor/ethanol, polyethylene glycol (PEG) 400, propylene glycol, Trappsol, alpha-cyclodextrin or analogs thereof, beta-cyclodextrin or analogs thereof, and gamma-cyclodextrin or analogs thereof.

14. The method of claim 1, wherein the subject is human.

15. A method of treating multiple myeloma in a subject comprising administering a pharmaceutical composition comprising a combination of a therapeutically effective amount of Beta-lapachone, or a derivative or analog thereof, and a taxane derivative or a derivative or analog.

16. The method of claim 15, wherein the taxane derivative is paclitaxel.

17. The method of claim 15, wherein the taxane derivative is administered intravenously.

18. The method of claim 15, wherein the taxane derivative is administered simultaneously with the Beta-lapachone.

19. The method of claim 15, wherein the taxane derivative is administered following administration of the Beta-lapachone.

20. The method of claim 15, wherein the taxane derivative is administered within 24 hours after the Beta-lapachone is administered.

21. The method of claim 15, wherein the therapeutically effective amount of the Beta-lapachone, or a derivative or analog thereof, is contained in a first vial, and the taxane derivative, or a derivative or analog thereof, is contained in a second vial, the contents of the first and second vials being administered to the patient simultaneously or sequentially.

22. The method of claim 21, wherein the Beta-lapachone, or a derivative or analog thereof in the first vial is Beta-lapachone, and the taxane derivative in the second vial is paclitaxel.

23. The method of claim 15, wherein the taxane derivative is administered intravenously at a dosage from approximately 135 mg/m$^2$ to about 300 mg/m$^2$.

24. The method of claim 15, wherein the taxane derivative is administered intravenously at a dosage of approximately 175 mg/m$^2$.

25. The method of claim 15, wherein the Beta-lapachone, or a derivative or analog thereof, and the taxane derivative, or a derivative or analog thereof, further comprises a pharmaceutically acceptable carrier.

26. The method of claim 25, wherein the pharmaceutically acceptable carrier is a water solubilizing carrier molecule selected from the group consisting of Poloxamer, Povidone K17, Povidone K12, Tween 80, ethanol, Cremophor/ethanol, polyethylene glycol (PEG) 400, propylene glycol, Trappsol, alpha-cyclodextrin or analogs thereof, beta-cyclodextrin or analogs thereof, and gamma-cyclodextrin or analogs thereof.

27. The method of claim 15, wherein the subject is human.

28. A method of treating multiple myeloma in a subject, the method comprising:
    a) administering to the subject a therapeutically effective amount of a Beta-lapachone, or a derivative or analog thereof and a pharmaceutically acceptable carrier;
    b) administering to the subject a therapeutically effective amount of a taxane derivative, or a derivative or analog thereof, the taxane derivative being administered simultaneously with, or following the Beta-lapachone.

29. The method of claim 28, wherein the taxane derivative is paclitaxel.

30. The method of claim 28, wherein the Beta-lapachone or a derivative or analog thereof, and the taxane derivative or a derivative or analog thereof are administered intravenously.

31. The method of claim 28, wherein the taxane derivative is administered simultaneously with the Beta-lapachone.

32. The method of claim 28, wherein the taxane derivative is administered following administration of the Beta-lapachone.

33. The method of claim 28, wherein the taxane derivative is administered within 24 hours after the Beta-lapachone is administered.

34. The method of claim 28, wherein the therapeutically effective amount of the Beta-lapachone, or a derivative or analog thereof, is contained in a first vial, and the taxane derivative, or a derivative or analog thereof, is contained in a second vial, the contents of the first and second vials being administered to the patient simultaneously or sequentially.

35. The method of claim 34, wherein the Beta-lapachone, or a derivative or analog thereof in the first vial is Beta-lapachone, and the taxane derivative in the second vial is paclitaxel.

36. The method of claim 28, wherein the taxane derivative is administered intravenously at a dosage from approximately 135 mg/m$^2$ to about 300 mg/m$^2$.

37. The method of claim 36, wherein the taxane derivative is administered intravenously at a dosage of approximately 175 mg/m$^2$.

38. The method of claim 28, wherein the Beta-lapachone, or a derivative or analog thereof, and the taxane derivative, or a derivative or analog thereof, further comprises a pharmaceutically acceptable carrier.

39. The method of claim 38, wherein the pharmaceutically acceptable carrier is a water solubilizing carrier molecule selected from the group consisting of Poloxamer, Povidone K17, Povidone K12, Tween 80, ethanol, Cremophor/ethanol, polyethylene glycol (PEG) 400, propylene glycol, Trappsol, alpha-cyclodextrin or analogs thereof, beta-cyclodextrin or analogs thereof, and gamma-cyclodextrin or analogs thereof.

40. The method of claim 28, wherein the subject is human.

41. The method of claim 1, wherein the Beta-lapachone or a derivative or analog thereof is administered intravenously.

42. The method of claim 15, wherein the Beta-lapachone or a derivative or analog thereof is administered intravenously.

43. The method of claim 1, wherein the Beta-lapachone or a derivative or analog thereof, further comprises a pharmaceutically acceptable polymer.

44. The method of claim 43, wherein the pharmaceutically acceptable polymer is selected from the group consisting of polyglutamic acid polymer, copolymers with polycaprolactone, polyglycolic acid, polyactic acid, polyacrylic acid, poly (2-hydroxyethyl 1-glutamine), carboxymethyl dextran, hyaluronic acid, human serum albumin and polyalginic acid or a combination thereof.

45. The method of claim 15, wherein the Beta-lapachone or a derivative or analog thereof, and the taxane derivative or a derivative or analog thereof, further comprises a pharmaceutically acceptable polymer.

46. The method of claim 45, wherein the pharmaceutically acceptable polymer is selected from the group consisting of polyglutamic acid polymer, copolymers with polycaprolactone, polyglycolic acid, polyactic acid, polyacrylic acid, poly (2-hydroxyethyl 1-glutamine), carboxymethyl dextran, hyaluronic acid, human serum albumin and polyalginic acid or a combination thereof.

47. The method of claim 28, wherein the Beta-lapachone or a derivative or analog thereof, and the taxane derivative or a derivative or analog thereof, further comprises a pharmaceutically acceptable polymer.

48. The method of claim 47, wherein the pharmaceutically acceptable polymer is selected from the group consisting of polyglutamic acid polymer, copolymers with polycaprolactone, polyglycolic acid, polyactic acid, polyacrylic acid, poly (2-hydroxyethyl 1-glutamine), carboxymethyl dextran, hyaluronic acid, human serum albumin and polyalginic acid or a combination thereof.

49. The method of claim 1, wherein the Beta-lapachone, or a derivative or analog thereof is Beta-lapachone.

50. The method of claim 15, wherein the Beta-lapachone, or a derivative or analog thereof is Beta-lapachone.

51. The method of claim 28, wherein the Beta-lapachone, or a derivative or analog thereof is Beta-lapachone.

* * * * *